US005620892A

United States Patent [19]

Kurtz et al.

[11] Patent Number: 5,620,892

[45] Date of Patent: Apr. 15, 1997

[54] **STRAIN OF *SACCHAROMYCES CEREVISIAE* EXPRESSING THE GENE ENCODING POTASSIUM TRANSPORTER MINK**

[75] Inventors: Stephen E. Kurtz, Princeton; Aron M. Knickerbocker, Titusville, both of N.J.; John R. McCullough, Newtown, Pa.

[73] Assignee: Bristol-Myers Squibb Company, Princeton, N.J.

[21] Appl. No.: 118,101

[22] Filed: Sep. 7, 1993

[51] Int. Cl.$^6$ .................... C12N 1/18; C12N 1/19

[52] U.S. Cl. .................... 435/354.21; 435/255.2; 536/23.5

[58] Field of Search .................... 435/255, 254, 435/256, 254.21, 255.2; 536/23.5

[56] References Cited

U.S. PATENT DOCUMENTS 5,208,145 5/1993 Rogers .................... 435/6

OTHER PUBLICATIONS

A. Rodriguez–Navarro et al., Journal of Bacteriology, vol. 159, No. 3, pp. 940–945, 1984.

R. F. Gaber et al., Molecular and Cellular Biology, vol. 8, pp. 2848–2859, 1988.

C. H. Ko et al., Genetics, vol. 125, pp. 305–312, 1990.

J. A. Anderson et al., Proc. Natl. Acad. Sci. USA, vol. 89,, pp. 3736–3740, 1992.

L. H. Phillipson et al., TIPS, vol. 13, pp. 8–11, 1992.

M. C. Sanguinetti et al., J. Gen. Physiol., vol. 96, pp. 195–215, 1990.

E. Honoré et al., The EMBO Journal, vol. 10, No. 10, pp. 2805–2811, 1991.

J. Ramos et al., Arch. Microbiol., vol. 143, pp. 88–93, 1985.

H. Sentenac et al., Science, vol. 256, pp. 663–665, 1992.

N. K. Jurkiewicz et al., Circulation Research, vol. 72, No. 1, pp. 75–83, 1993.

R. Swanson et al., Seminars in the Neuroscience, vol. 5, pp. 117–124, 1993.

M. Strong et al., Mol. Biol. Evol., vol. 10, No. 1, pp. 221–242, 1993.

T. Murai et al., Biochemical and Biophysical Research Communications, vol. 161, No. 1, pp. 176–181, 1989.

C. Ko et al., Molecular and Cellular Biology, vol. 11, No. 8, pp. 4266–4273, 1991.

B. Hille, Ionic Channels of Excitable Membranes, 2nd Edition, 1992 (tables of contents).

I. Ben–Efraim et al., Biochemistry, vol. 32, pp. 2371–2377, 1993.

L. Freeman et al., Biophysical J., vol. 64, No. 2, part 2, p. A341, 1993.

*Primary Examiner*—Keith D. Hendricks
*Attorney, Agent, or Firm*—Timothy J. Gaul

[57] ABSTRACT

A modified *Saccharomyces cerevisiae* cell, wherein the cell expresses minK but does not express TRK1 and TRK2. Also disclosed is a process for detecting modulators of minK, which comprises (a) treating such modified *Saccharomyces cerevisiae* cells with a test compound, (b) assessing growth in the presence of a test compound and (c) determining an increase or decrease in potassium uptake into the *Saccharomyces cerevisiae* cells. MinK inhibitors are useful anti-arrhythmic or antifibrillatory agents; activators, anti-ischemic agents.

10 Claims, 13 Drawing Sheets

```
181/1                                   211/11
ATG CAT TTT AGA AGA ACG ATG AGT AGA GTG CCC ACA TTG GCA TCT CTT GAA ATA CGA TAT
Met his phe arg arg thr met ser arg val pro thr leu ala ser leu glu ile arg tyr
241/21                                  271/31
AAA AAA TCT TTC GGC CAT AAA TTT CGT GAT TTT ATT GCT CTA TGT GGT CAC TAT TTT GCT
lys lys ser phe gly his lys phe arg asp phe ile ala leu cys gly his tyr phe ala
301/41                                  331/51
CCA GTT AAA AAA TAT ATC TTC CCC AGT TTT ATC GCG GTT CAC TAC TTC TAC ACG ATA TCC
pro val lys lys tyr ile phe pro ser phe ile ala val his tyr phe tyr thr ile ser
361/61                                  391/71
CTG ACA TTA ATA ACT TCA ATC CTG CTA TAT CCC ATT AAG AAT ACC AGA TAC ATT GAT ACA
leu thr leu ile thr ser ile leu leu tyr pro ile lys asn thr arg tyr ile asp thr
421/81                                  451/91
TTG TTT TTA GCA GCG GGC GCA GTT ACA CAA GGT GGC TTA AAT ACT GTG GAT ATC AAC AAT
leu phe leu ala ala gly ala val thr gln gly gly leu asn thr val asp ile asn asn
481/101                                 511/111
CTA AGC TTA TAC CAA CAA ATT GTT CTG TAT ATC GTA TGC TGC ATA TCA ACA CCA ATT GCA
leu ser leu tyr gln gln ile val leu tyr ile val cys cys ile ser thr pro ile ala
541/121                                 571/131
GTT CAT AGT TGC TTG GCA TTT GTA CGG CTT TAC TGG TTT GAG CGC TAC TTC GAT GGT ATT
val his ser cys leu ala phe val arg leu tyr trp phe glu arg tyr phe asp gly ile
601/141                                 631/151
AGA GAC TCT TCT AGA GCA AAT TTT AAG ATG AGA AGA ACG AAA ACA ATC TTA GAA AGG GAA
arg asp ser ser arg arg asn phe lys met arg arg thr lys thr ile leu glu arg glu
661/161                                 691/171
CTA ACA GCA AGA ACC ATG ACC AAG AAT AGA ACA GGT ACC CAA AGA ACG TCT TAT CCT AGG
leu thr ala arg thr met thr lys asn arg thr gly thr gln arg thr ser tyr pro arg
721/181                                 751/191
AAA CAA GCT AAA ACA GAT GAT TTC CAA GAA AAA TTG TTC AGC GGA GAA ATG GTT AAT AGA
lys gln ala lys thr asp asp phe gln glu lys leu phe ser gly glu met val asn arg
781/201                                 811/211
GAT GAG CAG GAC TCA GTT CAC AGC GAC CAG AAT TCT CAT GAC ATT AGT AGG GAC AGC AGC
asp glu gln asp ser val his ser asp gln asn ser his asp ile ser arg asp ser ser
841/221                                 871/231
AAT AAT AAT ACG AAT CAC AAT GGT AGC AGT GGC AGT TTA GAT GAT TTC GTT AAG GAA GAC
asn asn asn thr asn his asn gly ser ser gly ser leu asp asp phe val lys glu asp
901/241                                 931/251
GAA ACG GAT GAC AAT GGA GAA TAT CAG GAG AAC AAC TCC TAC TCG ACG GTA GGT AGT TCG
glu thr asp asp asn gly glu tyr gln glu asn asn ser tyr ser thr val gly ser ser
961/261                                 991/271
TCT AAC ACA GTT GCA GAC GAA AGT TTA AAT CAG AAG CCC AAG CCA AGC AGT CTT CGG TTT
ser asn thr val ala asp glu ser leu asn gln lys pro lys pro ser ser leu arg phe
1021/281                                1051/291
GAT GAG CCA CAC AGC AAA CAA AGA CCC GCA AGA GTT CCC TCA GAG AAA TTT GCA AAA AGA
asp glu pro his ser lys gln arg pro ala arg val pro ser glu lys phe ala lys arg
```

FIG. 2A

```
1081/301                                1111/311
AGG GGT TCA AGA GAT ATT AGC CCA GCC GAT ATG TAT CGA TCC ATT ATG ATG CTA CAA GGT
arg gly ser arg asp ile ser pro ala asp met tyr arg ser ile met met leu gln gly
1141/321                                1171/331
AAG CAT GAA GCA ACT GCT GAA GAT GAA GGT CCC CCT TTA GTC ATC GGG TCC CCT GCG GAT
lys his glu ala thr ala glu asp glu gly pro pro leu val ile gly ser pro ala asp
1201/341                                1231/351
GGC ACA AGA TAT AAA AGT AAT GTC AAT AAG CTA AAG AAG GCC ACC GGC ATA AAT GGT AAC
gly thr arg tyr lys ser asn val asn lys leu lys lys ala thr gly ile asn gly asn
1261/361                                1291/371
AAA ATC AAG ATT CGA GAT AAG GGA AAT GAA AGT AAC ACT GAT CAA AAT TCC GTG TCA AGT
lys ile lys ile arg asp lys gly asn glu ser asn thr asp gln asn ser val ser ser
1321/381                                1351/391
GAA GCA AAC AGT ACG GCG AGC GTT TCG GAC GAA AGC TCG TTA CAC ACA AAT TTT GGT AAC
glu ala asn ser thr ala ser val ser asp glu ser ser leu his thr asn phe gly asn
1381/401                                1411/411
AAA GTA CCT TCA TTA AGA ACA AAT ACT CAT AGA TCA AAT TCG GGC CCG ATA GCC ATT ACT
lys val pro ser leu arg thr asn thr his arg ser asn ser gly pro ile ala ile thr
1441/421                                1471/431
GAT AAC GCA GAA ACA GAC AAA AAG CAT GGG CCA TCA ATT CAA TTC GAT ATA ACT AAA CCT
asp asn ala glu thr asp lys lys his gly pro ser ile gln phe asp ile thr lys pro
1501/441                                1531/451
CCT AGA AAA ATT TCA AAA AGA GTT TCA ACC TTC GAT GAT TTG AAC CCA AAA TCT TCC GTT
pro arg lys ile ser lys arg val ser thr phe asp asp leu asn pro lys ser ser val
1561/461                                1591/471
CTT TAT CGA AAA AAA GCA TCG AAG AAG TAC CTC ATG AAA CAT TTT CCT AAA GCG CGG CGA
leu tyr arg lys lys ala ser lys lys tyr leu met lys his phe pro lys ala arg arg
1621/481                                1651/491
ATA CGG CAA CAA ATT AAG AGA AGG CTT TCT ACT GGT TCA ATT GAG AAA AAC AGC AGT AAC
ile arg gln gln ile lys arg arg leu ser thr gly ser ile glu lys asn ser ser asn
1681/501                                1711/511
AAT GTT TCA GAT AGA AAA CCT ATT ACT GAT ATG GAT GAT GAT GAT GAT GAC GAT GAC AAC
asn val ser asp arg lys pro ile thr asp met asp asp asp asp asp asp asp asp asn
1741/521                                1771/531
GAC GGC GAT AAC AAC GAA GAA TAC TTT GCT GAC AAC GAA AGC GGC GAT GAA GAT GAA CGA
asp gly asp asn asn glu glu tyr phe ala asp asn glu ser gly asp glu asp glu arg
1801/541                                1831/551
GTA CAG CAG TCT GAA CCA CAT TCT GAT TCA GAA CTC AAA TCG CAC CAA CAA CAG CAA GAA
val gln gln ser glu pro his ser asp ser glu leu lys ser his gln gln gln gln glu
1861/561                                1891/571
AAC CAC CAA CTG CAG CAG AAC CTG CAC CGC ATG TAT AAA ACC AAA TCA TTT GAT GAT AAT
lys his gln leu gln gln asn leu his arg met tyr lys thr lys ser phe asp asp asn
1921/581                                1951/591
CGT TCA AGA GCA GTT CCT ATG GAA CGT TCC AGG ACC ATC GAT ATG GCA GAG GCT AAG GAT
arg ser arg ala val pro met glu arg ser arg thr ile asp met ala glu ala lys asp
```

FIG. 2B

```
1981/601                                          2011/611
CTA AAT GAG CTC GCA AGG ACG CCT GAT TTT CAA AAA ATG GTC TAT CAA AAT TGG AAA GCC
leu asn glu leu ala arg thr pro asp phe gln lys met val tyr gln asn trp lys ala
2041/621                                          2071/631
CAT CAT AGA AAA AAA CCG AAC TTT AGG AAG AGG GGA TGG AAT AAC AAG ATA TTT GAA CAT
his his arg lys lys pro asn phe arg lys arg gly trp asn asn lys ile phe glu his
2101/641                                          2131/651
GGT CCC TAT GCA TCT GAC AGC GAT CGC AAT TAT CCT GAT AAT AGT AAT ACT GGA AAC AGT
gly pro tyr ala ser asp ser asp arg asn tyr pro asp asn ser asn thr gly asn ser
2161/661                                          2191/671
ATT CTT CAT TAC GCA GAG TCT ATT TTA CAT CAT GAT GGC TCT CAT AAA AAT GGA AGC GAA
ile leu his tyr ala glu ser ile leu his his asp gly ser his lys asn gly ser glu
2221/681                                          2251/691
GAA GCC TCT TCC GAC TCT AAT GAG AAT ATC TAT TCC ACG AAT GGA GGA AGC GAC CAC AAT
glu ala ser ser asp ser asn glu asn ile tyr ser thr asn gly gly ser asp his asn
2281/701                                          2311/711
GGT CTT AAC AAC TAT CCT ACT TAC AAC GAC GAT GAA GAA GGC TAT TAT GGT TTA CAT TTC
gly leu asn asn tyr pro thr tyr asn asp asp glu glu gly tyr tyr gly leu his phe
2341/721                                          2371/731
GAT ACC GAT TAT GAC CTA GAT CCT CGT CAT GAT TTA TCT AAA GGC AGT GGT AAA ACG TAT
asp thr asp tyr asp leu asp pro arg his asp leu ser lys gly ser gly lys thr tyr
2401/741                                          2431/751
CTA TCA TGG CAA CCA ACT ATT GGA CGT AAC TCA AAC TTC CTT GGA TTA ACA AGA GCC CAG
leu ser trp gln pro thr ile gly arg asn ser asn phe leu gly leu thr arg ala gln
2461/761                                          2491/771
AAA GAT GAA TTA GGT GGT GTC GAG TAC AGA GCA ATC AAA CTT TTA TGC ACC ATA TTG GTT
lys asp glu leu gly gly val glu tyr arg ala ile lys leu leu cys thr ile leu val
2521/781                                          2551/791
GTC TAC TAC GTT GGA TGG CAT ATT GTT GCT TTT GTT ATG TTA GTA CCT TGG ATT ATT TTG
val tyr tyr val gly trp his ile val ala phe val met leu val pro trp ile ile leu
2581/801                                          2611/811
AAA AAG CAT TAT AGT GAA GTT GTT AGA GAT GAT GGT GTT TCA CCT ACA TGG TGG GGA TTT
lys lys his tyr ser glu val val arg asp asp gly val ser pro thr trp trp gly phe
2641/821                                          2671/831
TGG ACA GCA ATG AGT GCA TTT AAT GAT TTA GGT TTG ACA TTA ACT CCA AAT TCA ATG ATG
trp thr ala met ser ala phe asn asp leu gly leu thr leu thr pro asn ser met met
2701/841                                          2731/851
TCG TTT AAC AAA GCT GTA TAC CCA TTG ATC GTT ATG ATT TGG TTT ATC ATT ATC GGA AAT
ser phe asn lys ala val tyr pro leu ile val met ile trp phe ile ile ile gly asn
2761/861                                          2791/871
ACA GGG TTT CCC ATC CTT CTT AGA TGC ATC ATT TGG ATA ATG TTT AAA ATT TCT CCT GAT
thr gly phe pro ile leu leu arg cys ile ile trp ile met phe lys ile ser pro asp
2821/881                                          2851/891
TTA TCA CAG ATG AGA GAA AGT TTA GGT TTT CTC TTA GAC CAT CCA CGT CGT TGT TTC ACC
leu ser gln met arg glu ser leu gly phe leu leu asp his pro arg arg cys phe thr
2881/901                                          2911/911
TTG CTA TTT CCT AAG GCA GCT ACA TGG TGG CTA CTT TTA ACG CTT GCA GGA TTG AAT ATA
leu leu phe pro lys ala ala thr trp trp leu leu leu thr leu ala gly leu asn ile
```

FIG. 2C

```
2941/921                                2971/931
ACT GAT TGG ATT TTA TTT ATT ATT CTA GAT TTT GGC TCA ACA GTT GTG AAA TCA TTA TCG
thr asp trp ile leu phe ile ile leu asp phe gly ser thr val val lys ser leu ser
3001/941                                3031/951
AAA GGC TAT AGA GTC CTT GTC GGC CTG TTT CAA TCT GTT AGC ACA AGA ACT GCT GGA TTC
lys gly tyr arg val leu val gly leu phe gln ser val ser thr arg thr ala gly phe
3061/961                                3091/971
AGC GTT GTC GAT TTA AGT CAA CTG CAT CCT TCT ATC CAA GTC TCC TAT ATG CTA ATG ATG
ser val val asp leu ser gln leu his pro ser ile gln val ser tyr met leu met met
3121/981                                3151/991
TAT GTC TCC GTA TTA CCA TTG GCC ATC TCT ATT CGA CGG ACA AAT GTT TAC GAG GAG CAA
tyr val ser val leu pro leu ala ile ser ile arg arg thr asn val tyr glu glu gln
3181/1001                               3211/1011
TCT TTA GGA CTA TAT GGA GAT ATG GGG GGA GAA CCA GAA GAT ACG GAT ACT GAA GAC GAT
ser leu gly leu tyr gly asp met gly gly glu pro glu asp thr asp thr glu asp asp
3241/1021                               3271/1031
GGT AAC GAT GAA GAT GAC GAC GAG GAA AAC GAG AGT CAC GAA GGT CAA AGT AGT CAA AGA
gly asn asp glu asp asp asp glu glu asn glu ser his glu gly gln ser ser gln arg
3301/1041                               3331/1051
AGT AGT TCG AAC AAC AAC AAC AAT AAC AAC AGG AAA AAG AAA AAG AAA AAG AAA ACT GAA
ser ser ser asn asn asn asn asn asn asn arg lys lys lys lys lys lys lys thr glu
3361/1061                               3391/1071
AAT CCA AAT GAA ATA TCT ACA AAA TCC TTT ATC GGT GCC CAT TTA AGG AAA CAG CTT TCA
asn pro asn glu ile ser thr lys ser phe ile gly ala his leu arg lys gln leu ser
3421/1081                               3451/1091
TTT GAC TTG TGG TTT CTA TTT TTA GGG TTA TTT ATC ATT TGC ATT TGT GAA GGG GAC AAG
phe asp leu trp phe leu phe leu gly leu phe ile ile cys ile cys glu gly asp lys
3481/1101                               3511/1111
ATA AAG GAC GTA CAA GAA CCA AAC TTT AAT ATA TTT GCA ATT CTT TTT GAA ATT GTT AGC
ile lys asp val gln glu pro asn phe asn ile phe ala ile leu phe glu ile val ser
3541/1121                               3571/1131
GCT TAC GGT ACA GTT GGG CTA TCG CTA GGT TAT CCG GAC ACC AAC CAA TCG TTT TCA AGA
ala tyr gly thr val gly leu ser leu gly tyr pro asp thr asn gln ser phe ser arg
3601/1141                               3631/1151
CAG TTT ACT ACA TTA TCT AAG TTG GTG ATC ATA GCT ATG CTG ATC AGA GGC AAG AAT AGA
gln phe thr thr leu ser lys leu val ile ile ala met leu ile arg gly lys asn arg
3661/1161                               3691/1171
GGT CTA CCA TAC TCA CTG GAT CGT GCA ATT ATC TTG CCT AGT GAT AGA CTT GAA CAT ATT
gly leu pro tyr ser leu asp arg ala ile ile leu pro ser asp arg leu glu his ile
3721/1181                               3751/1191
GAC CAC CTT GAG GGC ATG AAA TTG AAG AGA CAG GCT AGA ACC AAT ACA GAA GAC CCA ATG
asp his leu glu gly met lys leu lys arg gln ala arg thr asn thr glu asp pro met
3781/1201                               3811/1211
ACG GAA CAT TTC AAG AGA AGT TTC ACT GAT GTG AAA CAT CGT TGG GGA GCT CTT AAG CGT
thr glu his phe lys arg ser phe thr asp val lys his arg trp gly ala leu lys arg
3841/1221                               3871/1231
AAG ACC ACA CAT TCC CGA AAT CCT AAA AGG AGC AGC ACA ACG CTC TAA
lys thr thr his ser arg asn pro lys arg ser ser thr thr leu OCH
```

FIG. 2D

```
920/1                                   950/11
ATG CCA ACA GCT AAG AGG ACG TCA TCC AGG GCT TCG TTG GCA CTG CCC TTC CAG TTA CGG
Met pro thr ala lys arg thr ser ser arg ala ser leu ala leu pro phe gln leu arg
980/21                                  1010/31
TTG GTG CAC AAG AAA TCA TGG GGC CAT CGG CTA AGA GAC TTC ATT TCC GGG TTC TTA AAA
leu val his lys lys ser trp gly his arg leu arg asp phe ile ser gly phe leu lys
1040/41                                 1070/51
TCA TGC AGA CCC ATT GCT AAA TAC GTT TTC CCC AAC TTC ATC GTG GTG CAC TAT ATC TAC
ser cys arg pro ile ala lys tyr val phe pro asn phe ile val val his tyr ile tyr
1100/61                                 1130/71
CTG ATC ACG CTG TCG ATT ATC GGG TCC ATT CTG TTA TAT CCG TGC AAG AAC ACG GCG TTC
leu ile thr leu ser ile ile gly ser ile leu leu tyr pro cys lys asn thr ala phe
1160/81                                 1190/91
ATC GAT GTG CTA TTT CTG GCT GCT GGA GCG TCT ACA CAG GGC GGG CTG GCC ACC AAG AGC
ile asp val leu phe leu ala ala gly ala ser thr gln gly gly leu ala thr lys ser
1220/101                                1250/111
ACT AAC GAT TTC AAC CTG TAC CAG CAG ATA GTG GTG TAC GTC ATT ACA TTG CTG TCC ACG
thr asn asp phe asn leu tyr gln gln ile val val tyr val ile thr leu leu ser thr
1280/121                                1310/131
CCT ATA CTT ATT CAT GGG TTT TTG GCC TTT GTC AGG CTG TAT TGG TTT GAA AGG TAC TTC
pro ile leu ile his gly phe leu ala phe val arg leu tyr trp phe glu arg tyr phe
1340/141                                1370/151
GAC AAC ATT AGG GAT ATC TCC AAA CAG AAT TTT AAA CTA AGA AGG ACC ATG ACG TTG CAA
asp asn ile arg asp ile ser lys gln asn phe lys leu arg arg thr met thr leu gln
1400/161                                1430/171
CAA AGG GAA CTA TCG GGC AGC AGT GGC AAT GCC GCT CGA AGT AGG AGT TTC AAG GAC AAC
gln arg glu leu ser gly ser ser gly asn ala ala arg ser arg ser phe lys asp asn
1460/181                                1490/191
CTG TTC CGT GGG AAG TTT GTT TCC AGA GAA GAC CCA CGA CAA TCC GCT TCA GAT GTG CCG
leu phe arg gly lys phe val ser arg glu asp pro arg gln ser ala ser asp val pro
1520/201                                1550/211
ATG GAC TCT CCT GAC ACG TCC GCA TTG TCC TCA ATC TCA CCG TTG AAT GTT TCC TCC TCT
met asp ser pro asp thr ser ala leu ser ser ile ser pro leu asn val ser ser ser
1580/221                                1610/231
AAG GAG GAA TCC AGT GAC ACG CAA AGC TCG CCT CCA AAC TTC TCA AGT AAG CGC CAA CCC
lys glu glu ser ser asp thr gln ser ser pro pro asn phe ser ser lys arg gln pro
1640/241                                1670/251
TCA GAC GTT GAC CCA AGA GAC ATT TAC AAA TCG ATA ATG ATG CTA CAA AAA CAA CAA GAG
ser asp val asp pro arg asp ile tyr lys ser ile met met leu gln lys gln gln glu
```

FIG. 3A

```
1700/261                                1730/271
AAG AGC AAC GCA AAC TCC ACG GAT TCT TTT TCG AGC GAG ACC AAT GGA CCC GCT TTC ATT
lys ser asn ala asn ser thr asp ser phe ser ser glu thr asn gly pro ala phe ile
1760/281                                1790/291
GTG CAG GAA CGT CAT GAG AGA AGA GCC CCC CAC TGC TCA CTG AAA CGC CAT TCT GTC CTG
val gln glu arg his glu arg arg ala pro his cys ser leu lys arg his ser val leu
1820/301                                1850/311
CCA TCT TCT CAG GAA TTG AAC AAG CTA GCC CAG ACG AAA AGT TTC CAG AAA TTG CTT GGC
pro ser ser gln glu leu asn lys leu ala gln thr lys ser phe gln lys leu leu gly
1880/321                                1910/331
TTG CGG AGA GAT GAA GGT GAC CAT GAC TAC TTT GAC GGT GCT CCT CAC AAA TAT ATG GTC
leu arg arg asp glu gly asp his asp tyr phe asp gly ala pro his lys tyr met val
1940/341                                1970/351
ACC AAG AAG AAA AAA ATA TCT AGA ACG CAA TCA TGT AAC ATC CCA ACG TAT ACT GCT TCA
thr lys lys lys lys ile ser arg thr gln ser cys asn ile pro thr tyr thr ala ser
2000/361                                2030/371
CCG AGT CCT AAA ACC TCA GGC CAA GTA GTT GAA AAT CAT AGA AAC TTG GCC AAG TCG GCG
pro ser pro lys thr ser gly gln val val glu asn his arg asn leu ala lys ser ala
2060/381                                2090/391
CCT TCA TCT TTT GTT GAT GAG GAG ATG AGC TTT TCA CCG CAA GAG TCT TTG AAT TTA CAG
pro ser ser phe val asp glu glu met ser phe ser pro gln glu ser leu asn leu gln
2120/401                                2150/411
TTC CAA GCG CAC CCG CCC AAA CCA AAA CGA CGT GAA GGT GAT ATA GGC CAC CCC TTC ACC
phe gln ala his pro pro lys pro lys arg arg glu gly asp ile gly his pro phe thr
2180/421                                2210/431
AGA ACA ATG AGC ACC AAC TAT CTA TCG TGG CAG CCA ACC TTT GGC AGA AAC TCC GTC TTC
arg thr met ser thr asn tyr leu ser trp gln pro thr phe gly arg asn ser val phe
2240/441                                2270/451
ATT GGA CTC ACA AAG CAA CAA AAG GAG GAA CTC GGC GGT GTC GAA TAT CGT GCT TTG AGA
ile gly leu thr lys gln gln lys glu glu leu gly gly val glu tyr arg ala leu arg
2300/461                                2330/471
TTG CTG TGC TGC ATT CTC ATG GTA TAC TAC ATC GGA TTC AAC ATT TTG GCG TTT GTG ACC
leu leu cys cys ile leu met val tyr tyr ile gly phe asn ile leu ala phe val thr
2360/481                                2390/491
ATC GTT CCA TGG GCC TGT ACG AGG CAC CAC TAC TCA GAG ATT ATT AGA CGA AAT GGA GTT
ile val pro trp ala cys thr arg his his tyr ser glu ile ile arg arg asn gly val
2420/501                                2450/511
TCT CCA ACC TGG TGG GGG TTT TTC ACT GCA ATG AGT GCA TTC AGC AAC TTG GGT CTG TCT
ser pro thr trp trp gly phe phe thr ala met ser ala phe ser asn leu gly leu ser
```

FIG. 3B

```
2480/521                                2510/531
TTG ACC GCT GAT TCA ATG GTT TCC TTT GAT ACT GCG CCG TAT CCG CTG ATT TTC ATG ATG
leu thr ala asp ser met val ser phe asp thr ala pro tyr pro leu ile phe met met
2540/541                                2570/551
TTC TTC ATC ATC ATA GGC AAT ACA GGC TTC CCA ATT ATG TTA CGA TTT ATC ATT TGG ATC
phe phe ile ile ile gly asn thr gly phe pro ile met leu arg phe ile ile trp ile
2600/561                                2630/571
ATG TTC AAG ACC TCG AGA GAC CTA TCT CAG TTT AAG GAA AGT CTT GGG TTT CTC TTG GAT
met phe lys thr ser arg asp leu ser gln phe lys glu ser leu gly phe leu leu asp
2660/581                                2690/591
CAT CCG CGC AGG TGT TTT ACG TTG CTG TTC CCC AGC GGC CCC ACA TGG TGG CTG TTT ACA
his pro arg arg cys phe thr leu leu phe pro ser gly pro thr trp trp leu phe thr
2720/601                                2750/611
ACT TTA GTC GTC TTA AAC GCT ACG GAT TGG ATT CTT TTC ATA ATT CTG GAT TTC AAC TCC
thr leu val val leu asn ala thr asp trp ile leu phe ile ile leu asp phe asn ser
2780/621                                2810/631
GCT GTA GTA AGG CAG GTT GCT AAA GGT TAT CGA GCT CTC ATG GGC CTC TTC CAG TCT GTA
ala val val arg gln val ala lys gly tyr arg ala leu met gly leu phe gln ser val
2840/641                                2870/651
TGC ACA AGA ACT GCT GGA TTC AAC GTT GTT GAC TTA AGT AAA TTA CAC CCG TCC ATT CAG
cys thr arg thr ala gly phe asn val val asp leu ser lys leu his pro ser ile gln
2900/661                                2930/671
GTG TCT TAT ATG CTA ATG ATG TAC GTT TCG GTC CTG CCG CTG GCG ATT TCC ATT AGA AGA
val ser tyr met leu met met tyr val ser val leu pro leu ala ile ser ile arg arg
2960/681                                2990/691
ACG AAT GTT TAT GAG GAG CAA TCG TTG GGA CTA TAC GAT AGT GGA CAA GAT GAC GAA AAT
thr asn val tyr glu glu gln ser leu gly leu tyr asp ser gly gln asp asp glu asn
3020/701                                3050/711
ATC ACC CAC GAA GAC GAT ATA AAG GAA ACA GAC CAT GAT GGC GAA TCC GAA GAG CGA GAC
ile thr his glu asp asp ile lys glu thr asp his asp gly glu ser glu glu arg asp
3080/721                                3110/731
ACT GTA TCT ACA AAG TCC AAG CCG AAG AAA CAG TCC CCA AAA TCG TTT GTT GGT GCT CAT
thr val ser thr lys ser lys pro lys lys gln ser pro lys ser phe val gly ala his
3140/741                                3170/751
TTG AGG AGG CAA CTC TCT TTT GAT TTA TGG TAC CTA TTC CTT GGA TTA TTT ATA ATA TGC
leu arg arg gln leu ser phe asp leu trp tyr leu phe leu gly leu phe ile ile cys
3200/761                                3230/771
ATA TGC GAG GGC AGA AAA ATC GAA GAC GTT AAT AAA CCT GAT TTC AAT GTC TTT GCT ATA
ile cys glu gly arg lys ile glu asp val asn lys pro asp phe asn val phe ala ile
```

FIG. 3C

```
3260/781                                3290/791
TTG TTT GAA GTT GTT AGC GCT TAT GGT ACA GTG GGT TTG TCA TTG GGT TAC CCA AAC ACC
leu phe glu val val ser ala tyr gly thr val gly leu ser leu gly tyr pro asn thr
3320/801                                3350/811
AAC ACA TCA CTA TCT GCC CAG TTC ACC GTA TTA TCG AAG CTA GTC ATA ATT GCC ATG CTA
asn thr ser leu ser ala gln phe thr val leu ser lys leu val ile ile ala met leu
3380/821                                3410/831
ATA AGA GGA AGA AAT AGA GGT TTA CCA TAC ACT TTG GAT CGT GCC ATC ATG CTG CCA AGT
ile arg gly arg asn arg gly leu pro tyr thr leu asp arg ala ile met leu pro ser
3440/841                                3470/851
GAC AAA CTG GAA CAA ATT GAT CGT TTA CAA GAT ATG AAA GCT AAG GGT AAG TTG TTA GCC
asp lys leu glu gln ile asp arg leu gln asp met lys ala lys gly lys leu leu ala
3500/861                                3530/871
AAA GTT GGT GAG GAT CCA ATG ACT ACT TAC GTC AAA AAG AGA TCC CAC AAA CTG AAA AAA
lys val gly glu asp pro met thr thr tyr val lys lys arg ser his lys leu lys lys
3560/881
ATA GCA ACA AAG TTT TGG GGG AAG CAT TAA
ile ala thr lys phe trp gly lys his OCH
```

FIG. 3D

```
20/1                                    50/11
ATG CCC AGG ATG ATC CTG TCT AAC ACC ACA GCG GTG ACG CCC TTT CTG ACC AAG CTG TGG
Met pro arg met ile leu ser asn thr thr ala val thr pro phe leu thr lys leu trp
80/21                                   110/31
CAG GAG ACA GTT CAG CAG GGT GGC AAC ATG TCG GGC CTG GCC CGC AGG TCC CCC CGC AGC
gln glu thr val gln gln gly gly asn met ser gly leu ala arg arg ser pro arg ser
140/41                                  170/51
AGT GAC GGC AAG CTG GAG GCC CTC TAC GTC CTC ATG GTA CTG GGA TTC TTC GGC TTC TTC
ser asp gly lys leu glu ala leu tyr val leu met val leu gly phe phe gly phe phe
200/61                                  230/71
ACC CTG GGC ATC ATG CTG AGC TAC ATC CGC TCC AAG AAG CTG GAG CAC TCG AAC GAC CCA
thr leu gly ile met leu ser tyr ile arg ser lys lys leu glu his ser asn asp pro
260/81                                  290/91
TTC AAC GTC TAC ATC GAG TCC GAT GCC TGG CAA GAG AAG GAC AAG GCC TAT GTC CAG GCC
phe asn val tyr ile glu ser asp ala trp gln glu lys asp lys ala tyr val gln ala
320/101                                 350/111
CGG GTC CTG GAG AGC TAC AGG TCG TGC TAT GTC GTT GAA AAC CAT CTG GCC ATA GAA CAA
arg val leu glu ser tyr arg ser cys tyr val val glu asn his leu ala ile glu gln
380/121                                 410/131
CCC AAC ACA CAC CTT CCT GAG ACG AAG CCT TCC CCA TGA
pro asn thr his leu pro glu thr lys pro ser pro OPA
```

FIG. 4

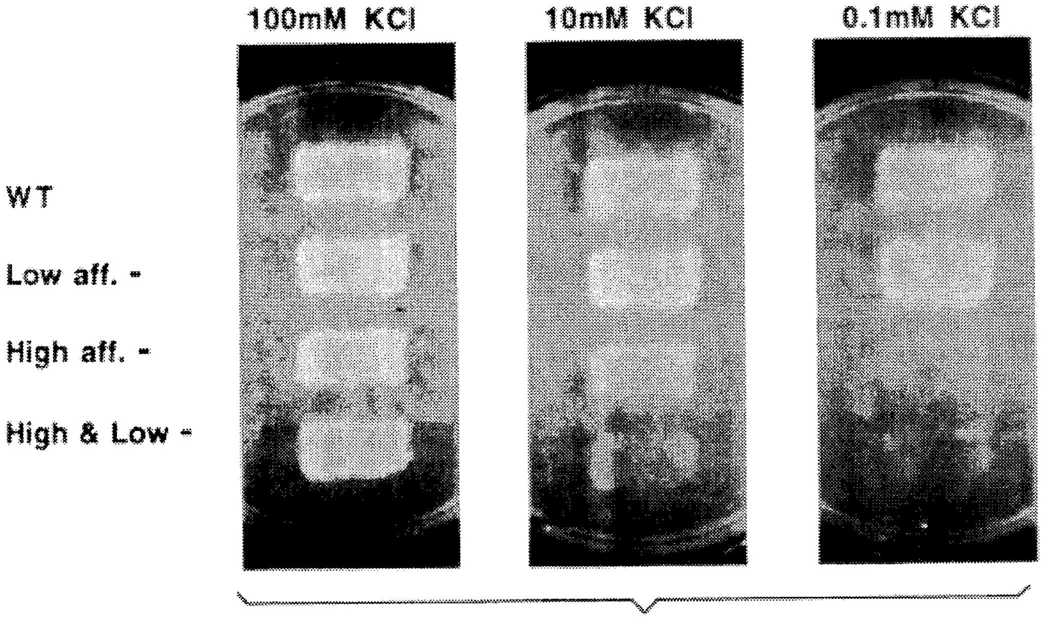
F I G. 5

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 3707 base pairs
( B ) TYPE: nucleic acid
( C ) STRANDEDNESS: single
( D ) TOPOLOGY: linear -continued ( i i ) MOLECULE TYPE: cDNA ( i x ) FEATURE:
( A ) NAME/KEY: CDS
( B ) LOCATION: 1..3707

( x i ) SEQUENCE DESCRIPTION: SEQ ID NO:1:

ATG CAT TTT AGA AGA ACG ATG AGT AGA GTG CCC ACA TTG GCA TCT CTT 48
Met His Phe Arg Arg Thr Met Ser Arg Val Pro Thr Leu Ala Ser Leu
1 5 10 15

GAA ATA CGA TAT AAA AAA TCT TTC GGC CAT AAA TTT CGT GAT TTT ATT 96
Glu Ile Arg Tyr Lys Lys Ser Phe Gly His Lys Phe Arg Asp Phe Ile
20 25 30

GCT CTA TGT GGT CAC TAT TTT GCT CCA GTT AAA AAA TAT ATC TTC CCC 144
Ala Leu Cys Gly His Tyr Phe Ala Pro Val Lys Lys Tyr Ile Phe Pro
35 40 45

AGT TTT ATC GCG GTT CAC TAC TTC TAC ACG ATA TCC CTG ACA TTA ATA 192
Ser Phe Ile Ala Val His Tyr Phe Tyr Thr Ile Ser Leu Thr Leu Ile
50 55 60

ACT TCA ATC CTG CTA TAT CCC ATT AAG AAT ACC AGA TAC ATT GAT ACA 240
Thr Ser Ile Leu Leu Tyr Pro Ile Lys Asn Thr Arg Tyr Ile Asp Thr
65 70 75 80

TTG TTT TTA GCA GCG GGC GCA GTT ACA CAA GGT GGC TTA AAT ACT GTG 288
Leu Phe Leu Ala Ala Gly Ala Val Thr Gln Gly Gly Leu Asn Thr Val
85 90 95

GAT ATC AAC AAT CTA AGC TTA TAC CAA CAA ATT GTT CTG TAT ATC GTA 336
Asp Ile Asn Asn Leu Ser Leu Tyr Gln Gln Ile Val Leu Tyr Ile Val
100 105 110

TGC TGC ATA TCA ACA CCA ATT GCA GTT CAT AGT TGC TTG GCA TTT GTA 384
Cys Cys Ile Ser Thr Pro Ile Ala Val His Ser Cys Leu Ala Phe Val
115 120 125

CGG CTT TAC TGG TTT GAG CGC TAC TTC GAT GGT ATT AGA GAC TCT TCT 432
Arg Leu Tyr Trp Phe Glu Arg Tyr Phe Asp Gly Ile Arg Asp Ser Ser
130 135 140

AGA CGA AAT TTT AAG ATG AGA AGA ACG AAA ACA ATC TTA GAA AGG GAA 480
Arg Arg Asn Phe Lys Met Arg Arg Thr Lys Thr Ile Leu Glu Arg Glu
145 150 155 160

CTA ACA GCA AGA ACC ATG ACC AAG AAT AGA ACA GGT ACC CAA AGA ACG 528
Leu Thr Ala Arg Thr Met Thr Lys Asn Arg Thr Gly Thr Gln Arg Thr
165 170 175

TCT TAT CCT AGG AAA CAA GCT AAA ACA GAT GAT TTC CAA GAA AAA TTG 576
Ser Tyr Pro Arg Lys Gln Ala Lys Thr Asp Asp Phe Gln Glu Lys Leu
180 185 190

TTC AGC GGA GAA ATG GTT AAT AGA GAT GAG CAG GAC TCA GTT CAC AGC 624
Phe Ser Gly Glu Met Val Asn Arg Asp Glu Gln Asp Ser Val His Ser
195 200 205

GAC CAG AAT TCT CAT GAC ATT AGT AGG GAC AGC AGC AAT AAT AAT ACG 672
Asp Gln Asn Ser His Asp Ile Ser Arg Asp Ser Ser Asn Asn Asn Thr
210 215 220

AAT CAC AAT GGT AGC AGT GGC AGT TTA GAT GAT TTC GTT AAG GAA GAC 720
Asn His Asn Gly Ser Ser Gly Ser Leu Asp Asp Phe Val Lys Glu Asp
225 230 235 240

GAA ACG GAT GAC AAT GGA GAA TAT CAG GAG AAC AAC TCC TAC TCG ACG 768
Glu Thr Asp Asp Asn Gly Glu Tyr Gln Glu Asn Asn Ser Tyr Ser Thr
245 250 255

GTA GGT AGT TCG TCT AAC ACA GTT GCA GAC GAA AGT TTA AAT CAG AAG 816
Val Gly Ser Ser Ser Asn Thr Val Ala Asp Glu Ser Leu Asn Gln Lys
260 265 270

CCC AAG CCA AGC AGT CTT CGG TTT GAT GAG CCA CAC AGC AAA CAA AGA 864
Pro Lys Pro Ser Ser Leu Arg Phe Asp Glu Pro His Ser Lys Gln Arg
275 280 285

-continued

```
CCC GCA AGA GTT CCC TCA GAG AAA TTT GCA AAA AGA AGG GGT TCA AGA   912
Pro Ala Arg Val Pro Ser Glu Lys Phe Ala Lys Arg Arg Gly Ser Arg
    290                 295                 300

GAT ATT AGC CCA GCC GAT ATG TAT CGA TCC ATT ATG ATG CTA CAA GGT   960
Asp Ile Ser Pro Ala Asp Met Tyr Arg Ser Ile Met Met Leu Gln Gly
305                 310                 315                 320

AAG CAT GAA GCA ACT GCT GAA GAT GAA GGT CCC CCT TTA GTC ATC GGG  1008
Lys His Glu Ala Thr Ala Glu Asp Glu Gly Pro Pro Leu Val Ile Gly
                325                 330                 335

TCC CCT GCG GAT GGC ACA AGA TAT AAA AGT AAT GTC AAT AAG CTA AAG  1056
Ser Pro Ala Asp Gly Thr Arg Tyr Lys Ser Asn Val Asn Lys Leu Lys
            340                 345                 350

AAG GCC ACC GGC ATA AAT GGT AAC AAA ATC AAG ATT CGA GAT AAG GGA  1104
Lys Ala Thr Gly Ile Asn Gly Asn Lys Ile Lys Ile Arg Asp Lys Gly
        355                 360                 365

AAT GAA AGT AAC ACT GAT CAA AAT TCC GTG TCA AGT GAA GCA AAC AGT  1152
Asn Glu Ser Asn Thr Asp Gln Asn Ser Val Ser Ser Glu Ala Asn Ser
    370                 375                 380

ACG GCG AGC GTT TCG GAC GAA AGC TCG TTA CAC ACA AAT TTT GGT AAC  1200
Thr Ala Ser Val Ser Asp Glu Ser Ser Leu His Thr Asn Phe Gly Asn
385                 390                 395                 400

AAA GTA CCT TCA TTA AGA ACA AAT ACT CAT AGA TCA AAT TCG GGC CCG  1248
Lys Val Pro Ser Leu Arg Thr Asn Thr His Arg Ser Asn Ser Gly Pro
                405                 410                 415

ATA GCC ATT ACT GAT AAC GCA GAA ACA GAC AAA AAG CAT GGG CCA TCA  1296
Ile Ala Ile Thr Asp Asn Ala Glu Thr Asp Lys Lys His Gly Pro Ser
            420                 425                 430

ATT CAA TTC GAT ATA ACT AAA CCT CCT AGA AAA ATT TCA AAA AGA GTT  1344
Ile Gln Phe Asp Ile Thr Lys Pro Pro Arg Lys Ile Ser Lys Arg Val
        435                 440                 445

TCA ACC TTC GAT GAT TTG AAC CCA AAA TCT TCC GTT CTT TAT CGA AAA  1392
Ser Thr Phe Asp Asp Leu Asn Pro Lys Ser Ser Val Leu Tyr Arg Lys
    450                 455                 460

AAA GCA TCG AAG AAG TAC CTC ATG AAA CAT TTT CCT AAA GCG CGG CGA  1440
Lys Ala Ser Lys Lys Tyr Leu Met Lys His Phe Pro Lys Ala Arg Arg
465                 470                 475                 480

ATA CGG CAA CAA ATT AAG AGA AGG CTT TCT ACT GGT TCA ATT GAG AAA  1488
Ile Arg Gln Gln Ile Lys Arg Arg Leu Ser Thr Gly Ser Ile Glu Lys
                485                 490                 495

AAC AGC AGT AAC AAT GTT TCA GAT AGA AAA CCT ATT ACT GAT ATG GAT  1536
Asn Ser Ser Asn Asn Val Ser Asp Arg Lys Pro Ile Thr Asp Met Asp
            500                 505                 510

GAT GAT GAT GAT GAC GAT GAC AAC GAC GGC GAT AAC AAC GAA GAA TAC  1584
Asp Asp Asp Asp Asp Asp Asp Asn Asp Gly Asp Asn Asn Glu Glu Tyr
        515                 520                 525

TTT GCT GAC AAC GAA AGC GGC GAT GAA GAT GAA CGA GTA CAG CAG TCT  1632
Phe Ala Asp Asn Glu Ser Gly Asp Glu Asp Glu Arg Val Gln Gln Ser
    530                 535                 540

GAA CCA CAT TCT GAT TCA GAA CTC AAA TCG CAC CAA CAA CAG CAA GAA  1680
Glu Pro His Ser Asp Ser Glu Leu Lys Ser His Gln Gln Gln Gln Glu
545                 550                 555                 560

AAA CAC CAA CTG CAG CAG AAC CTG CAC CGC ATG TAT AAA ACC AAA TCA  1728
Lys His Gln Leu Gln Gln Asn Leu His Arg Met Tyr Lys Thr Lys Ser
                565                 570                 575

TTT GAT GAT AAT CGT TCA AGA GCA GTT CCT ATG GAA CGT TCC AGG ACC  1776
Phe Asp Asp Asn Arg Ser Arg Ala Val Pro Met Glu Arg Ser Arg Thr
            580                 585                 590

ATC GAT ATG GCA GAG GCT AAG GAT CTA AAT GAG CTC GCA AGG ACG CCT  1824
Ile Asp Met Ala Glu Ala Lys Asp Leu Asn Glu Leu Ala Arg Thr Pro
        595                 600                 605
```

-continued

```
GAT TTT CAA AAA ATG GTC TAT CAA AAT TGG AAA GCC CAT CAT AGA AAA   1872
Asp Phe Gln Lys Met Val Tyr Gln Asn Trp Lys Ala His His Arg Lys
    610                 615                 620

AAA CCG AAC TTT AGG AAG AGG GGA TGG AAT AAC AAG ATA TTT GAA CAT   1920
Lys Pro Asn Phe Arg Lys Arg Gly Trp Asn Asn Lys Ile Phe Glu His
625                 630                 635                 640

GGT CCC TAT GCA TCT GAC AGC GAT CGC AAT TAT CCT GAT AAT AGT AAT   1968
Gly Pro Tyr Ala Ser Asp Ser Asp Arg Asn Tyr Pro Asp Asn Ser Asn
                645                 650                 655

ACT GGA AAC AGT ATT CTT CAT TAC GCA GAG TCT ATT TTA CAT CAT GAT   2016
Thr Gly Asn Ser Ile Leu His Tyr Ala Glu Ser Ile Leu His His Asp
            660                 665                 670

GGC TCT CAT AAA AAT GGA AGC GAA GAA GCC TCT TCC GAC TCT AAT GAG   2064
Gly Ser His Lys Asn Gly Ser Glu Glu Ala Ser Ser Asp Ser Asn Glu
        675                 680                 685

AAT ATC TAT TCC ACG AAT GGA GGA AGC GAC CAC AAT GGT CTT AAC AAC   2112
Asn Ile Tyr Ser Thr Asn Gly Gly Ser Asp His Asn Gly Leu Asn Asn
    690                 695                 700

TAT CCT ACT TAC AAC GAC GAT GAA GAA GGC TAT TAT GGT TTA CAT TTC   2160
Tyr Pro Thr Tyr Asn Asp Asp Glu Glu Gly Tyr Tyr Gly Leu His Phe
705                 710                 715                 720

GAT ACC GAT TAT GAC CTA GAT CCT CGT CAT GAT TTA TCT AAA GGC AGT   2208
Asp Thr Asp Tyr Asp Leu Asp Pro Arg His Asp Leu Ser Lys Gly Ser
                725                 730                 735

GGT AAA ACG TAT CTA TCA TGG CAA CCA ACT ATT GGA CGT AAC TCA AAC   2256
Gly Lys Thr Tyr Leu Ser Trp Gln Pro Thr Ile Gly Arg Asn Ser Asn
            740                 745                 750

TTC CTT GGA TTA ACA AGA GCC CAG AAA GAT GAA TTA GGT GGT GTC GAG   2304
Phe Leu Gly Leu Thr Arg Ala Gln Lys Asp Glu Leu Gly Gly Val Glu
        755                 760                 765

TAC AGA GCA ATC AAA CTT TTA TGC ACC ATA TTG GTT GTC TAC TAC GTT   2352
Tyr Arg Ala Ile Lys Leu Leu Cys Thr Ile Leu Val Val Tyr Tyr Val
    770                 775                 780

GGA TGG CAT ATT GTT GCT TTT GTT ATG TTA GTA CCT TGG ATT ATT TTG   2400
Gly Trp His Ile Val Ala Phe Val Met Leu Val Pro Trp Ile Ile Leu
785                 790                 795                 800

AAA AAG CAT TAT AGT GAA GTT GTT AGA GAT GAT GGT GTT TCA CCT ACA   2448
Lys Lys His Tyr Ser Glu Val Val Arg Asp Asp Gly Val Ser Pro Thr
                805                 810                 815

TGG TGG GGA TTT TGG ACA GCA ATG AGT GCA TTT AAT GAT TTA GGT TTG   2496
Trp Trp Gly Phe Trp Thr Ala Met Ser Ala Phe Asn Asp Leu Gly Leu
            820                 825                 830

ACA TTA ACT CCA AAT TCA ATG ATG TCG TTT AAC AAA GCT GTA TAC CCA   2544
Thr Leu Thr Pro Asn Ser Met Met Ser Phe Asn Lys Ala Val Tyr Pro
        835                 840                 845

TTG ATC GTT ATG ATT TGG TTT ATC ATT ATC GGA AAT ACA GGG TTT CCC   2592
Leu Ile Val Met Ile Trp Phe Ile Ile Ile Gly Asn Thr Gly Phe Pro
    850                 855                 860

ATC CTT CTT AGA TGC ATC ATT TGG ATA ATG TTT AAA ATT TCT CCT GAT   2640
Ile Leu Leu Arg Cys Ile Ile Trp Ile Met Phe Lys Ile Ser Pro Asp
865                 870                 875                 880

TTA TCA CAG ATG AGA GAA AGT TTA GGT TTT CTC TTA GAC CAT CCA CGT   2688
Leu Ser Gln Met Arg Glu Ser Leu Gly Phe Leu Leu Asp His Pro Arg
                885                 890                 895

CGT TGT TTC ACC TTG CTA TTT CCT AAG GCA GCT ACA TGG TGG CTA CTT   2736
Arg Cys Phe Thr Leu Leu Phe Pro Lys Ala Ala Thr Trp Trp Leu Leu
            900                 905                 910

TTA ACG CTT GCA GGA TTG AAT ATA ACT GAT TGG ATT TTA TTT ATT ATT   2784
Leu Thr Leu Ala Gly Leu Asn Ile Thr Asp Trp Ile Leu Phe Ile Ile
        915                 920                 925
```

-continued

CTA GAT TTT GGC TCA ACA GTT GTG AAA TCA TTA TCG AAA GGC TAT AGA 2832
Leu Asp Phe Gly Ser Thr Val Val Lys Ser Leu Ser Lys Gly Tyr Arg
930 935 940

GTC CTT GTC GGC CTG TTT CAA TCT GTT AGC ACA AGA ACT GCT GGA TTC 2880
Val Leu Val Gly Leu Phe Gln Ser Val Ser Thr Arg Thr Ala Gly Phe
945 950 955 960

AGC GTT GTC GAT TTA AGT CAA CTG CAT CCT TCT ATC CAA GTC TCC TAT 2928
Ser Val Val Asp Leu Ser Gln Leu His Pro Ser Ile Gln Val Ser Tyr
965 970 975

ATG CTA ATG ATG TAT GTC TCC GTA TTA CCA TTG GCC ATC TCT ATT CGA 2976
Met Leu Met Met Tyr Val Ser Val Leu Pro Leu Ala Ile Ser Ile Arg
980 985 990

CGG ACA AAT GTT TAC GAG GAG CAA TCT TTA GGA CTA TAT GGA GAT ATG 3024
Arg Thr Asn Val Tyr Glu Glu Gln Ser Leu Gly Leu Tyr Gly Asp Met
995 1000 1005

GGG GGA GAA CCA GAA GAT ACG GAT ACT GAA GAC GAT GGT AAC GAT GAA 3072
Gly Gly Glu Pro Glu Asp Thr Asp Thr Glu Asp Asp Gly Asn Asp Glu
1010 1015 1020

GAT GAC GAC GAG GAA AAC GAG AGT CAC GAA GGT CAA AGT AGT CAA AGA 3120
Asp Asp Asp Glu Glu Asn Glu Ser His Glu Gly Gln Ser Ser Gln Arg
1025 1030 1035 1040

AGT AGT TCG AAC AAC AAC AAC AAT AAC AAC AGG AAA AAG AAA AAG AAA 3168
Ser Ser Ser Asn Asn Asn Asn Asn Asn Asn Arg Lys Lys Lys Lys Lys
1045 1050 1055

AAG AAA ACT GAA AAT CCA AAT GAA ATA TCT ACA AAA TCC TTT ATC GGT 3216
Lys Lys Thr Glu Asn Pro Asn Glu Ile Ser Thr Lys Ser Phe Ile Gly
1060 1065 1070

GCC CAT TTA AGG AAA CAG CTT TCA TTT GAC TTG TGG TTT CTA TTT TTA 3264
Ala His Leu Arg Lys Gln Leu Ser Phe Asp Leu Trp Phe Leu Phe Leu
1075 1080 1085

GGG TTA TTT ATC ATT TGC ATT TGT GAA GGG GAC AAG ATA AAG GAC GTA 3312
Gly Leu Phe Ile Ile Cys Ile Cys Glu Gly Asp Lys Ile Lys Asp Val
1090 1095 1100

CAA GAA CCA AAC TTT AAT ATA TTT GCA ATT CTT TTT GAA ATT GTT AGC 3360
Gln Glu Pro Asn Phe Asn Ile Phe Ala Ile Leu Phe Glu Ile Val Ser
1105 1110 1115 1120

GCT TAC GGT ACA GTT GGG CTA TCG CTA GGT TAT CCG GAC ACC AAC CAA 3408
Ala Tyr Gly Thr Val Gly Leu Ser Leu Gly Tyr Pro Asp Thr Asn Gln
1125 1130 1135

TCG TTT TCA AGA CAG TTT ACT ACA TTA TCT AAG TTG GTG ATC ATA GCT 3456
Ser Phe Ser Arg Gln Phe Thr Thr Leu Ser Lys Leu Val Ile Ile Ala
1140 1145 1150

ATG CTG ATC AGA GGC AAG AAT AGA GGT CTA CCA TAC TCA CTG GAT CGT 3504
Met Leu Ile Arg Gly Lys Asn Arg Gly Leu Pro Tyr Ser Leu Asp Arg
1155 1160 1165

GCA ATT ATC TTG CCT AGT GAT AGA CTT GAA CAT ATT GAC CAC CTT GAG 3552
Ala Ile Ile Leu Pro Ser Asp Arg Leu Glu His Ile Asp His Leu Glu
1170 1175 1180

GGC ATG AAA TTG AAG AGA CAG GCT AGA ACC AAT ACA GAA GAC CCA ATG 3600
Gly Met Lys Leu Lys Arg Gln Ala Arg Thr Asn Thr Glu Asp Pro Met
1185 1190 1195 1200

ACG GAA CAT TTC AAG AGA AGT TTC ACT GAT GTG AAA CAT CGT TGG GGA 3648
Thr Glu His Phe Lys Arg Ser Phe Thr Asp Val Lys His Arg Trp Gly
1205 1210 1215

GCT CTT AAG CGT AAG ACC ACA CAT TCC CGA AAT CCT AAA AGG AGC AGC 3696
Ala Leu Lys Arg Lys Thr Thr His Ser Arg Asn Pro Lys Arg Ser Ser
1220 1225 1230

ACA ACG CTC TA 3707
Thr Thr Leu
123

( 2 ) INFORMATION FOR SEQ ID NO:2:

( i ) SEQUENCE CHARACTERISTICS:
( A ) LENGTH: 1235 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met His Phe Arg Arg Thr Met Ser Arg Val Pro Thr Leu Ala Ser Leu
  1               5                  10                  15

Glu Ile Arg Tyr Lys Lys Ser Phe Gly His Lys Phe Arg Asp Phe Ile
            20                  25                  30

Ala Leu Cys Gly His Tyr Phe Ala Pro Val Lys Lys Tyr Ile Phe Pro
        35                  40                  45

Ser Phe Ile Ala Val His Tyr Phe Tyr Thr Ile Ser Leu Thr Leu Ile
    50                  55                  60

Thr Ser Ile Leu Leu Tyr Pro Ile Lys Asn Thr Arg Tyr Ile Asp Thr
 65                  70                  75                  80

Leu Phe Leu Ala Ala Gly Ala Val Thr Gln Gly Gly Leu Asn Thr Val
                 85                  90                  95

Asp Ile Asn Asn Leu Ser Leu Tyr Gln Gln Ile Val Leu Tyr Ile Val
            100                 105                 110

Cys Cys Ile Ser Thr Pro Ile Ala Val His Ser Cys Leu Ala Phe Val
        115                 120                 125

Arg Leu Tyr Trp Phe Glu Arg Tyr Phe Asp Gly Ile Arg Asp Ser Ser
    130                 135                 140

Arg Arg Asn Phe Lys Met Arg Arg Thr Lys Thr Ile Leu Glu Arg Glu
145                 150                 155                 160

Leu Thr Ala Arg Thr Met Thr Lys Asn Arg Thr Gly Thr Gln Arg Thr
                165                 170                 175

Ser Tyr Pro Arg Lys Gln Ala Lys Thr Asp Asp Phe Gln Glu Lys Leu
            180                 185                 190

Phe Ser Gly Glu Met Val Asn Arg Asp Glu Gln Asp Ser Val His Ser
        195                 200                 205

Asp Gln Asn Ser His Asp Ile Ser Arg Asp Ser Ser Asn Asn Asn Thr
    210                 215                 220

Asn His Asn Gly Ser Ser Gly Ser Leu Asp Asp Phe Val Lys Glu Asp
225                 230                 235                 240

Glu Thr Asp Asp Asn Gly Glu Tyr Gln Glu Asn Asn Ser Tyr Ser Thr
                245                 250                 255

Val Gly Ser Ser Ser Asn Thr Val Ala Asp Glu Ser Leu Asn Gln Lys
            260                 265                 270

Pro Lys Pro Ser Ser Leu Arg Phe Asp Glu Pro His Ser Lys Gln Arg
        275                 280                 285

Pro Ala Arg Val Pro Ser Glu Lys Phe Ala Lys Arg Arg Gly Ser Arg
    290                 295                 300

Asp Ile Ser Pro Ala Asp Met Tyr Arg Ser Ile Met Met Leu Gln Gly
305                 310                 315                 320

Lys His Glu Ala Thr Ala Glu Asp Glu Gly Pro Pro Leu Val Ile Gly
                325                 330                 335

Ser Pro Ala Asp Gly Thr Arg Tyr Lys Ser Asn Val Asn Lys Leu Lys
            340                 345                 350

Lys Ala Thr Gly Ile Asn Gly Asn Lys Ile Lys Ile Arg Asp Lys Gly
        355                 360                 365
```

-continued

| | | | | | | | | | | | | | | | |
|---|---|---|---|---|---|---|---|---|---|---|---|---|---|---|---|
| Asn | Glu | Ser | Asn | Thr | Asp | Gln | Asn | Ser | Val | Ser | Ser | Glu | Ala | Asn | Ser |
| | 370 | | | | | 375 | | | | | 380 | | | | |
| Thr | Ala | Ser | Val | Ser | Asp | Glu | Ser | Ser | Leu | His | Thr | Asn | Phe | Gly | Asn |
| 385 | | | | | 390 | | | | | 395 | | | | | 400 |
| Lys | Val | Pro | Ser | Leu | Arg | Thr | Asn | Thr | His | Arg | Ser | Asn | Ser | Gly | Pro |
| | | | | 405 | | | | | 410 | | | | | 415 | |
| Ile | Ala | Ile | Thr | Asp | Asn | Ala | Glu | Thr | Asp | Lys | Lys | His | Gly | Pro | Ser |
| | | | 420 | | | | | 425 | | | | | 430 | | |
| Ile | Gln | Phe | Asp | Ile | Thr | Lys | Pro | Pro | Arg | Lys | Ile | Ser | Lys | Arg | Val |
| | | 435 | | | | | 440 | | | | | 445 | | | |
| Ser | Thr | Phe | Asp | Asp | Leu | Asn | Pro | Lys | Ser | Ser | Val | Leu | Tyr | Arg | Lys |
| | 450 | | | | | 455 | | | | | 460 | | | | |
| Lys | Ala | Ser | Lys | Lys | Tyr | Leu | Met | Lys | His | Phe | Pro | Lys | Ala | Arg | Arg |
| 465 | | | | | 470 | | | | | 475 | | | | | 480 |
| Ile | Arg | Gln | Gln | Ile | Lys | Arg | Arg | Leu | Ser | Thr | Gly | Ser | Ile | Glu | Lys |
| | | | | 485 | | | | | 490 | | | | | 495 | |
| Asn | Ser | Ser | Asn | Asn | Val | Ser | Asp | Arg | Lys | Pro | Ile | Thr | Asp | Met | Asp |
| | | | 500 | | | | | 505 | | | | | 510 | | |
| Asp | Asp | Asp | Asp | Asp | Asp | Asp | Asn | Asp | Gly | Asp | Asn | Asn | Glu | Glu | Tyr |
| | | 515 | | | | | 520 | | | | | 525 | | | |
| Phe | Ala | Asp | Asn | Glu | Ser | Gly | Asp | Glu | Asp | Glu | Arg | Val | Gln | Gln | Ser |
| | 530 | | | | | 535 | | | | | 540 | | | | |
| Glu | Pro | His | Ser | Asp | Ser | Glu | Leu | Lys | Ser | His | Gln | Gln | Gln | Gln | Glu |
| 545 | | | | | 550 | | | | | 555 | | | | | 560 |
| Lys | His | Gln | Leu | Gln | Gln | Asn | Leu | His | Arg | Met | Tyr | Lys | Thr | Lys | Ser |
| | | | | 565 | | | | | 570 | | | | | 575 | |
| Phe | Asp | Asp | Asn | Arg | Ser | Arg | Ala | Val | Pro | Met | Glu | Arg | Ser | Arg | Thr |
| | | | 580 | | | | | 585 | | | | | 590 | | |
| Ile | Asp | Met | Ala | Glu | Ala | Lys | Asp | Leu | Asn | Glu | Leu | Ala | Arg | Thr | Pro |
| | | 595 | | | | | 600 | | | | | 605 | | | |
| Asp | Phe | Gln | Lys | Met | Val | Tyr | Gln | Asn | Trp | Lys | Ala | His | His | Arg | Lys |
| | 610 | | | | | 615 | | | | | 620 | | | | |
| Lys | Pro | Asn | Phe | Arg | Lys | Arg | Gly | Trp | Asn | Asn | Lys | Ile | Phe | Glu | His |
| 625 | | | | | 630 | | | | | 635 | | | | | 640 |
| Gly | Pro | Tyr | Ala | Ser | Asp | Ser | Asp | Arg | Asn | Tyr | Pro | Asp | Asn | Ser | Asn |
| | | | | 645 | | | | | 650 | | | | | 655 | |
| Thr | Gly | Asn | Ser | Ile | Leu | His | Tyr | Ala | Glu | Ser | Ile | Leu | His | His | Asp |
| | | | 660 | | | | | 665 | | | | | 670 | | |
| Gly | Ser | His | Lys | Asn | Gly | Ser | Glu | Glu | Ala | Ser | Ser | Asp | Ser | Asn | Glu |
| | | 675 | | | | | 680 | | | | | 685 | | | |
| Asn | Ile | Tyr | Ser | Thr | Asn | Gly | Gly | Ser | Asp | His | Asn | Gly | Leu | Asn | Asn |
| | 690 | | | | | 695 | | | | | 700 | | | | |
| Tyr | Pro | Thr | Tyr | Asn | Asp | Asp | Glu | Glu | Gly | Tyr | Tyr | Gly | Leu | His | Phe |
| 705 | | | | | 710 | | | | | 715 | | | | | 720 |
| Asp | Thr | Asp | Tyr | Asp | Leu | Asp | Pro | Arg | His | Asp | Leu | Ser | Lys | Gly | Ser |
| | | | | 725 | | | | | 730 | | | | | 735 | |
| Gly | Lys | Thr | Tyr | Leu | Ser | Trp | Gln | Pro | Thr | Ile | Gly | Arg | Asn | Ser | Asn |
| | | | 740 | | | | | 745 | | | | | 750 | | |
| Phe | Leu | Gly | Leu | Thr | Arg | Ala | Gln | Lys | Asp | Glu | Leu | Gly | Gly | Val | Glu |
| | | 755 | | | | | 760 | | | | | 765 | | | |
| Tyr | Arg | Ala | Ile | Lys | Leu | Leu | Cys | Thr | Ile | Leu | Val | Val | Tyr | Tyr | Val |
| | 770 | | | | | 775 | | | | | 780 | | | | |
| Gly | Trp | His | Ile | Val | Ala | Phe | Val | Met | Leu | Val | Pro | Trp | Ile | Ile | Leu |

-continued 785 790 795 800

Lys Lys His Tyr Ser Glu Val Val Arg Asp Asp Gly Val Ser Pro Thr
805 810 815

Trp Trp Gly Phe Trp Thr Ala Met Ser Ala Phe Asn Asp Leu Gly Leu
820 825 830

Thr Leu Thr Pro Asn Ser Met Met Ser Phe Asn Lys Ala Val Tyr Pro
835 840 845

Leu Ile Val Met Ile Trp Phe Ile Ile Ile Gly Asn Thr Gly Phe Pro
850 855 860

Ile Leu Leu Arg Cys Ile Ile Trp Ile Met Phe Lys Ile Ser Pro Asp
865 870 875 880

Leu Ser Gln Met Arg Glu Ser Leu Gly Phe Leu Leu Asp His Pro Arg
885 890 895

Arg Cys Phe Thr Leu Leu Phe Pro Lys Ala Ala Thr Trp Trp Leu Leu
900 905 910

Leu Thr Leu Ala Gly Leu Asn Ile Thr Asp Trp Ile Leu Phe Ile Ile
915 920 925

Leu Asp Phe Gly Ser Thr Val Val Lys Ser Leu Ser Lys Gly Tyr Arg
930 935 940

Val Leu Val Gly Leu Phe Gln Ser Val Ser Thr Arg Thr Ala Gly Phe
945 950 955 960

Ser Val Val Asp Leu Ser Gln Leu His Pro Ser Ile Gln Val Ser Tyr
965 970 975

Met Leu Met Met Tyr Val Ser Val Leu Pro Leu Ala Ile Ser Ile Arg
980 985 990

Arg Thr Asn Val Tyr Glu Glu Gln Ser Leu Gly Leu Tyr Gly Asp Met
995 1000 1005

Gly Gly Glu Pro Glu Asp Thr Asp Thr Glu Asp Asp Gly Asn Asp Glu
1010 1015 1020

Asp Asp Asp Glu Glu Asn Glu Ser His Glu Gly Gln Ser Ser Gln Arg
1025 1030 1035 1040

Ser Ser Ser Asn Asn Asn Asn Asn Asn Asn Arg Lys Lys Lys Lys Lys
1045 1050 1055

Lys Lys Thr Glu Asn Pro Asn Glu Ile Ser Thr Lys Ser Phe Ile Gly
1060 1065 1070

Ala His Leu Arg Lys Gln Leu Ser Phe Asp Leu Trp Phe Leu Phe Leu
1075 1080 1085

Gly Leu Phe Ile Ile Cys Ile Cys Glu Gly Asp Lys Ile Lys Asp Val
1090 1095 1100

Gln Glu Pro Asn Phe Asn Ile Phe Ala Ile Leu Phe Glu Ile Val Ser
1105 1110 1115 1120

Ala Tyr Gly Thr Val Gly Leu Ser Leu Gly Tyr Pro Asp Thr Asn Gln
1125 1130 1135

Ser Phe Ser Arg Gln Phe Thr Thr Leu Ser Lys Leu Val Ile Ile Ala
1140 1145 1150

Met Leu Ile Arg Gly Lys Asn Arg Gly Leu Pro Tyr Ser Leu Asp Arg
1155 1160 1165

Ala Ile Ile Leu Pro Ser Asp Arg Leu Glu His Ile Asp His Leu Glu
1170 1175 1180

Gly Met Lys Leu Lys Arg Gln Ala Arg Thr Asn Thr Glu Asp Pro Met
1185 1190 1195 1200

Thr Glu His Phe Lys Arg Ser Phe Thr Asp Val Lys His Arg Trp Gly
1205 1210 1215

```
Ala Leu Lys Arg Lys Thr Thr His Ser Arg Asn Pro Lys Arg Ser Ser
            1220                1225                1230

Thr Thr Leu
        1235
```

( 2 ) INFORMATION FOR SEQ ID NO:3:

( i ) SEQUENCE CHARACTERISTICS:
( A ) LENGTH: 2669 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..2669

( x i ) SEQUENCE DESCRIPTION: SEQ ID NO:3:

```
ATG CCA ACA GCT AAG AGG ACG TCA TCC AGG GCT TCG TTG GCA CTG CCC      48
Met Pro Thr Ala Lys Arg Thr Ser Ser Arg Ala Ser Leu Ala Leu Pro
  1               5                  10                  15

TTC CAG TTA CGG TTG GTG CAC AAG AAA TCA TGG GGC CAT CGG CTA AGA      96
Phe Gln Leu Arg Leu Val His Lys Lys Ser Trp Gly His Arg Leu Arg
             20                  25                  30

GAC TTC ATT TCC GGG TTC TTA AAA TCA TGC AGA CCC ATT GCT AAA TAC     144
Asp Phe Ile Ser Gly Phe Leu Lys Ser Cys Arg Pro Ile Ala Lys Tyr
         35                  40                  45

GTT TTC CCC AAC TTC ATC GTG GTG CAC TAT ATC TAC CTG ATC ACG CTG     192
Val Phe Pro Asn Phe Ile Val Val His Tyr Ile Tyr Leu Ile Thr Leu
     50                  55                  60

TCG ATT ATC GGG TCC ATT CTG TTA TAT CCG TGC AAG AAC ACG GCG TTC     240
Ser Ile Ile Gly Ser Ile Leu Leu Tyr Pro Cys Lys Asn Thr Ala Phe
 65                  70                  75                  80

ATC GAT GTG CTA TTT CTG GCT GCT GGA GCG TCT ACA CAG GGC GGG CTG     288
Ile Asp Val Leu Phe Leu Ala Ala Gly Ala Ser Thr Gln Gly Gly Leu
                 85                  90                  95

GCC ACC AAG AGC ACT AAC GAT TTC AAC CTG TAC CAG CAG ATA GTG GTG     336
Ala Thr Lys Ser Thr Asn Asp Phe Asn Leu Tyr Gln Gln Ile Val Val
            100                 105                 110

TAC GTC ATT ACA TTG CTG TCC ACG CCT ATA CTT ATT CAT GGG TTT TTG     384
Tyr Val Ile Thr Leu Leu Ser Thr Pro Ile Leu Ile His Gly Phe Leu
        115                 120                 125

GCC TTT GTC AGG CTG TAT TGG TTT GAA AGG TAC TTC GAC AAC ATT AGG     432
Ala Phe Val Arg Leu Tyr Trp Phe Glu Arg Tyr Phe Asp Asn Ile Arg
    130                 135                 140

GAT ATC TCC AAA CAG AAT TTT AAA CTA AGA AGG ACC ATG ACG TTG CAA     480
Asp Ile Ser Lys Gln Asn Phe Lys Leu Arg Arg Thr Met Thr Leu Gln
145                 150                 155                 160

CAA AGG GAA CTA TCG GGC AGC AGT GGC AAT GCC GCT CGA AGT AGG AGT     528
Gln Arg Glu Leu Ser Gly Ser Ser Gly Asn Ala Ala Arg Ser Arg Ser
                165                 170                 175

TTC AAG GAC AAC CTG TTC CGT GGG AAG TTT GTT TCC AGA GAA GAC CCA     576
Phe Lys Asp Asn Leu Phe Arg Gly Lys Phe Val Ser Arg Glu Asp Pro
            180                 185                 190

CGA CAA TCC GCT TCA GAT GTG CCG ATG GAC TCT CCT GAC ACG TCC GCA     624
Arg Gln Ser Ala Ser Asp Val Pro Met Asp Ser Pro Asp Thr Ser Ala
        195                 200                 205

TTG TCC TCA ATC TCA CCG TTG AAT GTT TCC TCC TCT AAG GAG GAA TCC     672
Leu Ser Ser Ile Ser Pro Leu Asn Val Ser Ser Ser Lys Glu Glu Ser
    210                 215                 220

AGT GAC ACG CAA AGC TCG CCT CCA AAC TTC TCA AGT AAG CGC CAA CCC     720
```

-continued

Ser Asp Thr Gln Ser Ser Pro Pro Asn Phe Ser Ser Lys Arg Gln Pro
225 230 235 240

TCA GAC GTT GAC CCA AGA GAC ATT TAC AAA TCG ATA ATG ATG CTA CAA 768
Ser Asp Val Asp Pro Arg Asp Ile Tyr Lys Ser Ile Met Met Leu Gln
245 250 255

AAA CAA CAA GAG AAG AGC AAC GCA AAC TCC ACG GAT TCT TTT TCG AGC 816
Lys Gln Gln Glu Lys Ser Asn Ala Asn Ser Thr Asp Ser Phe Ser Ser
260 265 270

GAG ACC AAT GGA CCC GCT TTC ATT GTG CAG GAA CGT CAT GAG AGA AGA 864
Glu Thr Asn Gly Pro Ala Phe Ile Val Gln Glu Arg His Glu Arg Arg
275 280 285

GCC CCC CAC TGC TCA CTG AAA CGC CAT TCT GTC CTG CCA TCT TCT CAG 912
Ala Pro His Cys Ser Leu Lys Arg His Ser Val Leu Pro Ser Ser Gln
290 295 300

GAA TTG AAC AAG CTA GCC CAG ACG AAA AGT TTC CAG AAA TTG CTT GGC 960
Glu Leu Asn Lys Leu Ala Gln Thr Lys Ser Phe Gln Lys Leu Leu Gly
305 310 315 320

TTG CGG AGA GAT GAA GGT GAC CAT GAC TAC TTT GAC GGT GCT CCT CAC 1008
Leu Arg Arg Asp Glu Gly Asp His Asp Tyr Phe Asp Gly Ala Pro His
325 330 335

AAA TAT ATG GTC ACC AAG AAG AAA AAA ATA TCT AGA ACG CAA TCA TGT 1056
Lys Tyr Met Val Thr Lys Lys Lys Lys Ile Ser Arg Thr Gln Ser Cys
340 345 350

AAC ATC CCA ACG TAT ACT GCT TCA CCG AGT CCT AAA ACC TCA GGC CAA 1104
Asn Ile Pro Thr Tyr Thr Ala Ser Pro Ser Pro Lys Thr Ser Gly Gln
355 360 365

GTA GTT GAA AAT CAT AGA AAC TTG GCC AAG TCG GCG CCT TCA TCT TTT 1152
Val Val Glu Asn His Arg Asn Leu Ala Lys Ser Ala Pro Ser Ser Phe
370 375 380

GTT GAT GAG GAG ATG AGC TTT TCA CCG CAA GAG TCT TTG AAT TTA CAG 1200
Val Asp Glu Glu Met Ser Phe Ser Pro Gln Glu Ser Leu Asn Leu Gln
385 390 395 400

TTC CAA GCG CAC CCG CCC AAA CCA AAA CGA CGT GAA GGT GAT ATA GGC 1248
Phe Gln Ala His Pro Pro Lys Pro Lys Arg Arg Glu Gly Asp Ile Gly
405 410 415

CAC CCC TTC ACC AGA ACA ATG AGC ACC AAC TAT CTA TCG TGG CAG CCA 1296
His Pro Phe Thr Arg Thr Met Ser Thr Asn Tyr Leu Ser Trp Gln Pro
420 425 430

ACC TTT GGC AGA AAC TCC GTC TTC ATT GGA CTC ACA AAG CAA CAA AAG 1344
Thr Phe Gly Arg Asn Ser Val Phe Ile Gly Leu Thr Lys Gln Gln Lys
435 440 445

GAG GAA CTC GGC GGT GTC GAA TAT CGT GCT TTG AGA TTG CTG TGC TGC 1392
Glu Glu Leu Gly Gly Val Glu Tyr Arg Ala Leu Arg Leu Leu Cys Cys
450 455 460

ATT CTC ATG GTA TAC TAC ATC GGA TTC AAC ATT TTG GCG TTT GTG ACC 1440
Ile Leu Met Val Tyr Tyr Ile Gly Phe Asn Ile Leu Ala Phe Val Thr
465 470 475 480

ATC GTT CCA TGG GCC TGT ACG AGG CAC CAC TAC TCA GAG ATT ATT AGA 1488
Ile Val Pro Trp Ala Cys Thr Arg His His Tyr Ser Glu Ile Ile Arg
485 490 495

CGA AAT GGA GTT TCT CCA ACC TGG TGG GGG TTT TTC ACT GCA ATG AGT 1536
Arg Asn Gly Val Ser Pro Thr Trp Trp Gly Phe Phe Thr Ala Met Ser
500 505 510

GCA TTC AGC AAC TTG GGT CTG TCT TTG ACC GCT GAT TCA ATG GTT TCC 1584
Ala Phe Ser Asn Leu Gly Leu Ser Leu Thr Ala Asp Ser Met Val Ser
515 520 525

TTT GAT ACT GCG CCG TAT CCG CTG ATT TTC ATG ATG TTC TTC ATC ATC 1632
Phe Asp Thr Ala Pro Tyr Pro Leu Ile Phe Met Met Phe Phe Ile Ile
530 535 540

ATA GGC AAT ACA GGC TTC CCA ATT ATG TTA CGA TTT ATC ATT TGG ATC 1680

-continued

```
Ile Gly Asn Thr Gly Phe Pro Ile Met Leu Arg Phe Ile Ile Trp Ile
545                 550                 555                 560

ATG TTC AAG ACC TCG AGA GAC CTA TCT CAG TTT AAG GAA AGT CTT GGG   1728
Met Phe Lys Thr Ser Arg Asp Leu Ser Gln Phe Lys Glu Ser Leu Gly
                565                 570                 575

TTT CTC TTG GAT CAT CCG CGC AGG TGT TTT ACG TTG CTG TTC CCC AGC   1776
Phe Leu Leu Asp His Pro Arg Arg Cys Phe Thr Leu Leu Phe Pro Ser
            580                 585                 590

GGC CCC ACA TGG TGG CTG TTT ACA ACT TTA GTC GTC TTA AAC GCT ACG   1824
Gly Pro Thr Trp Trp Leu Phe Thr Thr Leu Val Val Leu Asn Ala Thr
        595                 600                 605

GAT TGG ATT CTT TTC ATA ATT CTG GAT TTC AAC TCC GCT GTA GTA AGG   1872
Asp Trp Ile Leu Phe Ile Ile Leu Asp Phe Asn Ser Ala Val Val Arg
    610                 615                 620

CAG GTT GCT AAA GGT TAT CGA GCT CTC ATG GGC CTC TTC CAG TCT GTA   1920
Gln Val Ala Lys Gly Tyr Arg Ala Leu Met Gly Leu Phe Gln Ser Val
625                 630                 635                 640

TGC ACA AGA ACT GCT GGA TTC AAC GTT GTT GAC TTA AGT AAA TTA CAC   1968
Cys Thr Arg Thr Ala Gly Phe Asn Val Val Asp Leu Ser Lys Leu His
                645                 650                 655

CCG TCC ATT CAG GTG TCT TAT ATG CTA ATG ATG TAC GTT TCG GTC CTG   2016
Pro Ser Ile Gln Val Ser Tyr Met Leu Met Met Tyr Val Ser Val Leu
            660                 665                 670

CCG CTG GCG ATT TCC ATT AGA AGA ACG AAT GTT TAT GAG GAG CAA TCG   2064
Pro Leu Ala Ile Ser Ile Arg Arg Thr Asn Val Tyr Glu Glu Gln Ser
        675                 680                 685

TTG GGA CTA TAC GAT AGT GGA CAA GAT GAC GAA AAT ATC ACC CAC GAA   2112
Leu Gly Leu Tyr Asp Ser Gly Gln Asp Asp Glu Asn Ile Thr His Glu
    690                 695                 700

GAC GAT ATA AAG GAA ACA GAC CAT GAT GGC GAA TCC GAA GAG CGA GAC   2160
Asp Asp Ile Lys Glu Thr Asp His Asp Gly Glu Ser Glu Glu Arg Asp
705                 710                 715                 720

ACT GTA TCT ACA AAG TCC AAG CCG AAG AAA CAG TCC CCA AAA TCG TTT   2208
Thr Val Ser Thr Lys Ser Lys Pro Lys Lys Gln Ser Pro Lys Ser Phe
                725                 730                 735

GTT GGT GCT CAT TTG AGG AGG CAA CTC TCT TTT GAT TTA TGG TAC CTA   2256
Val Gly Ala His Leu Arg Arg Gln Leu Ser Phe Asp Leu Trp Tyr Leu
            740                 745                 750

TTC CTT GGA TTA TTT ATA ATA TGC ATA TGC GAG GGC AGA AAA ATC GAA   2304
Phe Leu Gly Leu Phe Ile Ile Cys Ile Cys Glu Gly Arg Lys Ile Glu
        755                 760                 765

GAC GTT AAT AAA CCT GAT TTC AAT GTC TTT GCT ATA TTG TTT GAA GTT   2352
Asp Val Asn Lys Pro Asp Phe Asn Val Phe Ala Ile Leu Phe Glu Val
    770                 775                 780

GTT AGC GCT TAT GGT ACA GTG GGT TTG TCA TTG GGT TAC CCA AAC ACC   2400
Val Ser Ala Tyr Gly Thr Val Gly Leu Ser Leu Gly Tyr Pro Asn Thr
785                 790                 795                 800

AAC ACA TCA CTA TCT GCC CAG TTC ACC GTA TTA TCG AAG CTA GTC ATA   2448
Asn Thr Ser Leu Ser Ala Gln Phe Thr Val Leu Ser Lys Leu Val Ile
                805                 810                 815

ATT GCC ATG CTA ATA AGA GGA AGA AAT AGA GGT TTA CCA TAC ACT TTG   2496
Ile Ala Met Leu Ile Arg Gly Arg Asn Arg Gly Leu Pro Tyr Thr Leu
            820                 825                 830

GAT CGT GCC ATC ATG CTG CCA AGT GAC AAA CTG GAA CAA ATT GAT CGT   2544
Asp Arg Ala Ile Met Leu Pro Ser Asp Lys Leu Glu Gln Ile Asp Arg
        835                 840                 845

TTA CAA GAT ATG AAA GCT AAG GGT AAG TTG TTA GCC AAA GTT GGT GAG   2592
Leu Gln Asp Met Lys Ala Lys Gly Lys Leu Leu Ala Lys Val Gly Glu
    850                 855                 860

GAT CCA ATG ACT ACT TAC GTC AAA AAG AGA TCC CAC AAA CTG AAA AAA   2640
```

```
Asp Pro Met Thr Thr Tyr Val Lys Lys Arg Ser His Lys Leu Lys Lys
865                 870                 875                 880

ATA GCA ACA AAG TTT TGG GGG AAG CAT TA                                2669
Ile Ala Thr Lys Phe Trp Gly Lys His
                885
```

( 2 ) INFORMATION FOR SEQ ID NO:4:

( i ) SEQUENCE CHARACTERISTICS:
( A ) LENGTH: 889 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Pro Thr Ala Lys Arg Thr Ser Ser Arg Ala Ser Leu Ala Leu Pro
  1             5                  10                  15

Phe Gln Leu Arg Leu Val His Lys Lys Ser Trp Gly His Arg Leu Arg
            20                  25                  30

Asp Phe Ile Ser Gly Phe Leu Lys Ser Cys Arg Pro Ile Ala Lys Tyr
        35                  40                  45

Val Phe Pro Asn Phe Ile Val Val His Tyr Ile Tyr Leu Ile Thr Leu
    50                  55                  60

Ser Ile Ile Gly Ser Ile Leu Leu Tyr Pro Cys Lys Asn Thr Ala Phe
 65                  70                  75                  80

Ile Asp Val Leu Phe Leu Ala Ala Gly Ala Ser Thr Gln Gly Gly Leu
                85                  90                  95

Ala Thr Lys Ser Thr Asn Asp Phe Asn Leu Tyr Gln Gln Ile Val Val
           100                 105                 110

Tyr Val Ile Thr Leu Leu Ser Thr Pro Ile Leu Ile His Gly Phe Leu
       115                 120                 125

Ala Phe Val Arg Leu Tyr Trp Phe Glu Arg Tyr Phe Asp Asn Ile Arg
   130                 135                 140

Asp Ile Ser Lys Gln Asn Phe Lys Leu Arg Arg Thr Met Thr Leu Gln
145                 150                 155                 160

Gln Arg Glu Leu Ser Gly Ser Ser Gly Asn Ala Ala Arg Ser Arg Ser
               165                 170                 175

Phe Lys Asp Asn Leu Phe Arg Gly Lys Phe Val Ser Arg Glu Asp Pro
           180                 185                 190

Arg Gln Ser Ala Ser Asp Val Pro Met Asp Ser Pro Asp Thr Ser Ala
       195                 200                 205

Leu Ser Ser Ile Ser Pro Leu Asn Val Ser Ser Ser Lys Glu Glu Ser
   210                 215                 220

Ser Asp Thr Gln Ser Ser Pro Pro Asn Phe Ser Ser Lys Arg Gln Pro
225                 230                 235                 240

Ser Asp Val Asp Pro Arg Asp Ile Tyr Lys Ser Ile Met Met Leu Gln
               245                 250                 255

Lys Gln Gln Glu Lys Ser Asn Ala Asn Ser Thr Asp Ser Phe Ser Ser
           260                 265                 270

Glu Thr Asn Gly Pro Ala Phe Ile Val Gln Glu Arg His Glu Arg Arg
       275                 280                 285

Ala Pro His Cys Ser Leu Lys Arg His Ser Val Leu Pro Ser Ser Gln
   290                 295                 300

Glu Leu Asn Lys Leu Ala Gln Thr Lys Ser Phe Gln Lys Leu Leu Gly
305                 310                 315                 320

Leu Arg Arg Asp Glu Gly Asp His Asp Tyr Phe Asp Gly Ala Pro His
```

-continued

```
                325                 330                 335

Lys Tyr Met Val Thr Lys Lys Lys Lys Ile Ser Arg Thr Gln Ser Cys
            340                 345                 350

Asn Ile Pro Thr Tyr Thr Ala Ser Pro Ser Pro Lys Thr Ser Gly Gln
        355                 360                 365

Val Val Glu Asn His Arg Asn Leu Ala Lys Ser Ala Pro Ser Ser Phe
    370                 375                 380

Val Asp Glu Glu Met Ser Phe Ser Pro Gln Glu Ser Leu Asn Leu Gln
385                 390                 395                 400

Phe Gln Ala His Pro Pro Lys Pro Lys Arg Arg Glu Gly Asp Ile Gly
                405                 410                 415

His Pro Phe Thr Arg Thr Met Ser Thr Asn Tyr Leu Ser Trp Gln Pro
            420                 425                 430

Thr Phe Gly Arg Asn Ser Val Phe Ile Gly Leu Thr Lys Gln Gln Lys
        435                 440                 445

Glu Glu Leu Gly Gly Val Glu Tyr Arg Ala Leu Arg Leu Leu Cys Cys
    450                 455                 460

Ile Leu Met Val Tyr Tyr Ile Gly Phe Asn Ile Leu Ala Phe Val Thr
465                 470                 475                 480

Ile Val Pro Trp Ala Cys Thr Arg His His Tyr Ser Glu Ile Ile Arg
                485                 490                 495

Arg Asn Gly Val Ser Pro Thr Trp Trp Gly Phe Phe Thr Ala Met Ser
            500                 505                 510

Ala Phe Ser Asn Leu Gly Leu Ser Leu Thr Ala Asp Ser Met Val Ser
        515                 520                 525

Phe Asp Thr Ala Pro Tyr Pro Leu Ile Phe Met Met Phe Phe Ile Ile
    530                 535                 540

Ile Gly Asn Thr Gly Phe Pro Ile Met Leu Arg Phe Ile Ile Trp Ile
545                 550                 555                 560

Met Phe Lys Thr Ser Arg Asp Leu Ser Gln Phe Lys Glu Ser Leu Gly
                565                 570                 575

Phe Leu Leu Asp His Pro Arg Arg Cys Phe Thr Leu Leu Phe Pro Ser
            580                 585                 590

Gly Pro Thr Trp Trp Leu Phe Thr Thr Leu Val Val Leu Asn Ala Thr
        595                 600                 605

Asp Trp Ile Leu Phe Ile Ile Leu Asp Phe Asn Ser Ala Val Val Arg
    610                 615                 620

Gln Val Ala Lys Gly Tyr Arg Ala Leu Met Gly Leu Phe Gln Ser Val
625                 630                 635                 640

Cys Thr Arg Thr Ala Gly Phe Asn Val Val Asp Leu Ser Lys Leu His
                645                 650                 655

Pro Ser Ile Gln Val Ser Tyr Met Leu Met Met Tyr Val Ser Val Leu
            660                 665                 670

Pro Leu Ala Ile Ser Ile Arg Arg Thr Asn Val Tyr Glu Glu Gln Ser
        675                 680                 685

Leu Gly Leu Tyr Asp Ser Gly Gln Asp Asp Glu Asn Ile Thr His Glu
    690                 695                 700

Asp Asp Ile Lys Glu Thr Asp His Asp Gly Glu Ser Glu Glu Arg Asp
705                 710                 715                 720

Thr Val Ser Thr Lys Ser Lys Pro Lys Lys Gln Ser Pro Lys Ser Phe
                725                 730                 735

Val Gly Ala His Leu Arg Arg Gln Leu Ser Phe Asp Leu Trp Tyr Leu
            740                 745                 750
```

-continued

```
Phe Leu Gly Leu Phe Ile Ile Cys Ile Cys Glu Gly Arg Lys Ile Glu
        755                 760                 765

Asp Val Asn Lys Pro Asp Phe Asn Val Phe Ala Ile Leu Phe Glu Val
    770                 775                 780

Val Ser Ala Tyr Gly Thr Val Gly Leu Ser Leu Gly Tyr Pro Asn Thr
785                 790                 795                 800

Asn Thr Ser Leu Ser Ala Gln Phe Thr Val Leu Ser Lys Leu Val Ile
                805                 810                 815

Ile Ala Met Leu Ile Arg Gly Arg Asn Arg Gly Leu Pro Tyr Thr Leu
            820                 825                 830

Asp Arg Ala Ile Met Leu Pro Ser Asp Lys Leu Glu Gln Ile Asp Arg
        835                 840                 845

Leu Gln Asp Met Lys Ala Lys Gly Lys Leu Leu Ala Lys Val Gly Glu
    850                 855                 860

Asp Pro Met Thr Thr Tyr Val Lys Lys Arg Ser His Lys Leu Lys Lys
865                 870                 875                 880

Ile Ala Thr Lys Phe Trp Gly Lys His
                885
```

( 2 ) INFORMATION FOR SEQ ID NO:5:

( i ) SEQUENCE CHARACTERISTICS:
( A ) LENGTH: 398 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..398

( x i ) SEQUENCE DESCRIPTION: SEQ ID NO:5:

```
ATG CCC AGG ATG ATC CTG TCT AAC ACC ACA GCG GTG ACG CCC TTT CTG      48
Met Pro Arg Met Ile Leu Ser Asn Thr Thr Ala Val Thr Pro Phe Leu
  1               5                  10                  15

ACC AAG CTG TGG CAG GAG ACA GTT CAG CAG GGT GGC AAC ATG TCG GGC      96
Thr Lys Leu Trp Gln Glu Thr Val Gln Gln Gly Gly Asn Met Ser Gly
             20                  25                  30

CTG GCC CGC AGG TCC CCC CGC AGC AGT GAC GGC AAG CTG GAG GCC CTC     144
Leu Ala Arg Arg Ser Pro Arg Ser Ser Asp Gly Lys Leu Glu Ala Leu
         35                  40                  45

TAC GTC CTC ATG GTA CTG GGA TTC TTC GGC TTC TTC ACC CTG GGC ATC     192
Tyr Val Leu Met Val Leu Gly Phe Phe Gly Phe Phe Thr Leu Gly Ile
     50                  55                  60

ATG CTG AGC TAC ATC CGC TCC AAG AAG CTG GAG CAC TCG AAC GAC CCA     240
Met Leu Ser Tyr Ile Arg Ser Lys Lys Leu Glu His Ser Asn Asp Pro
 65                  70                  75                  80

TTC AAC GTC TAC ATC GAG TCC GAT GCC TGG CAA GAG AAG GAC AAG GCC     288
Phe Asn Val Tyr Ile Glu Ser Asp Ala Trp Gln Glu Lys Asp Lys Ala
                 85                  90                  95

TAT GTC CAG GCC CGG GTC CTG GAG AGC TAC AGG TCG TGC TAT GTC GTT     336
Tyr Val Gln Ala Arg Val Leu Glu Ser Tyr Arg Ser Cys Tyr Val Val
            100                 105                 110

GAA AAC CAT CTG GCC ATA GAA CAA CCC AAC ACA CAC CTT CCT GAG ACG     384
Glu Asn His Leu Ala Ile Glu Gln Pro Asn Thr His Leu Pro Glu Thr
        115                 120                 125

AAG CCT TCC CCA TG                                                  398
Lys Pro Ser Pro
    130
```

( 2 ) INFORMATION FOR SEQ ID NO:6:

( i ) SEQUENCE CHARACTERISTICS:
( A ) LENGTH: 132 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Pro Arg Met Ile Leu Ser Asn Thr Thr Ala Val Thr Pro Phe Leu
1 5 10 15

Thr Lys Leu Trp Gln Glu Thr Val Gln Gln Gly Gly Asn Met Ser Gly
20 25 30

Leu Ala Arg Arg Ser Pro Arg Ser Ser Asp Gly Lys Leu Glu Ala Leu
35 40 45

Tyr Val Leu Met Val Leu Gly Phe Phe Gly Phe Phe Thr Leu Gly Ile
50 55 60

Met Leu Ser Tyr Ile Arg Ser Lys Lys Leu Glu His Ser Asn Asp Pro
65 70 75 80

Phe Asn Val Tyr Ile Glu Ser Asp Ala Trp Gln Glu Lys Asp Lys Ala
85 90 95

Tyr Val Gln Ala Arg Val Leu Glu Ser Tyr Arg Ser Cys Tyr Val Val
100 105 110

Glu Asn His Leu Ala Ile Glu Gln Pro Asn Thr His Leu Pro Glu Thr
115 120 125

Lys Pro Ser Pro
130

( 2 ) INFORMATION FOR SEQ ID NO:7:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

CCGGATCCAT GCATTTTAGA AGAACGATG 29

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

ATCGGCATGC GTTGACGATG ACGAAAGCAC 30

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA -continued ( x i ) SEQUENCE DESCRIPTION: SEQ ID NO:9:

GCGGATCCGT CGACTTCATT TCCGGGTTCT 30

( 2 ) INFORMATION FOR SEQ ID NO:10:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

GCTAGGAGCT CCCGGGTTGG CGCTTACTTG AGAA 34

( 2 ) INFORMATION FOR SEQ ID NO:11:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

GTCTTAAACG CTACGGATTG GATTC 25

( 2 ) INFORMATION FOR SEQ ID NO:12:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

GCTTCCCCCA AAACTTTGTT GC 22

( 2 ) INFORMATION FOR SEQ ID NO:13:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

GCGAATTCAA AAAAAATGAT CCTGTCTAAC ACCAC 35

( 2 ) INFORMATION FOR SEQ ID NO:14:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:14:

GCTCTAGATC ATGGGGAAGG CTTCGTCTC 29

-continued ( 2 ) INFORMATION FOR SEQ ID NO:15:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:15:

CGGGATCCAA AAAATGCATT TTAGAAGAAC GATGAG 36

( 2 ) INFORMATION FOR SEQ ID NO:16:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:16:

CCCGCTCGAG CGATGAGTGG GGATTTTGTC 30

STRAIN OF *SACCHAROMYCES CEREVISIAE* EXPRESSING THE GENE ENCODING POTASSIUM TRANSPORTER MINK

FIELD OF THE INVENTION

This invention relates to yeast, recombinant DNA techniques, and to processes for detecting inhibitors and/or activators of potassium channels.

BACKGROUND OF THE INVENTION

The uptake of potassium ions in yeast cells occurs primarily through two specific proteins—a high and a low affinity potassium ion transporter. Rodriguez-Navarro and Ramos, *J. Bacteriol,* 159:940–945 (1984); Gaber, Styles, and Fink, *Mol. Cell Biol.* 8:2848–2859 (1988); Ko and Gaber, *Genetics* 125: 305–312 (1990). Two genes, designated TRK1 and TRK2 (for transporter of K) encode the high and low affinity transporters, respectively. Yeast strains that contain mutations in TRK1 and TRK2 exhibit a growth defect on media with minimal potassium ion ($K^+$) concentrations. In comparison to wild-type strains, which grow on media with as little as 5 μM potassium ion, transporter mutant strains require media supplemented with 100 mM potassium ion. Two laboratories used such deficient strains to isolate foreign plant genes that complement the growth defect on potassium-deficient media. Anderson, et al., *Proc. Natl. Acad. Sci. U.S.A.* 89: 3736–3740 (1992); Sentenac, et al., *Science* 256: 663–666 (1992).

In other species, a number of potassium channels have been cloned by molecular biological techniques. Many of these cloned channels are voltage-dependent potassium ion channels related to the Drosophila shaker channel. Several others are novel potassium ion channels. Hille, *Ionic Channels of Excitable Membranes* (1992); Strong et al., *Mol. Biol. Evol.* 10: 221–242 (1993).

One such newly discovered channel is the minK, or $I_{sk}$, or $IK_s$, channel, which has only 129–130 amino acids. Murai et al., *Bioch. Biophys. Res. Comm.* 161: 176–181 (1989); Swanson et al., *Sem. Neurosci.* 5: 117–124 (1993). A recent report indicates that residues 41 to 72 define the pore of the protein and are sufficient to form channels in lipid bilayers. Ben-Efraim et al., *Biochemistry* 32: 2371–2377 (1993). The channel minK displays very slow activation and inactivation kinetics. Philipson and Miller, *TIPS* 13:8–11 (1992). It is expressed in a number of tissues, including kidney, uterus and heart and in a number of species including humans. Swanson et al., *Sem. Neurosci.* 5: 117–124 (1993); Freeman and Kass, *Biophysical J.* 64: 342 (abstract) (1993).

Of considerable interest is the role of minK in the heart. It was known that ventricular cells have a repolarzing current, called the delayed rectifier. Recent evidence suggests that the delayed rectifier has two components: a rapid, rectifying component, $I_{Kr}$, and a slow component, $I_{Ks}$. Sanguinetti and Jurkiewicz, *J. Gen Physiol.* 96:195–215 (1990). $I_{Kr}$ is blocked by such Class III antiarrhythmics as d-sotalol, dofetilide, and clofilium; $I_{Ks}$, in contrast, is blocked by clofilium but not by d-sotalol or dofetilide. Honore et al., *EMBO J.* 10:2805–2811 (1990); Jurkiewicz and Sanguinetti, *Circ. Res.* 72: 75–83 (1993). When expressed in Xenopus oocytes, minK exhibits kinetics and pharmacology similar to those of $I_{Ks}$ found in isolated myocytes, including blockage by clofilium. Honore et al., *EMBO J.* 10:2805–2811 (1991 ); Adelman, personal communication. Immunological detection of minK protein in cells possessing $I_{Ks}$ has recently been reported. Freeman and Kass, *Biophys. J.* 64:342 (abstract) (1993). These results suggest that the minK product is the slow component of the delayed rectifier.

At faster heart rates, $I_{Ks}$ contributes to the shortening of the action potential observed at rapid heart rates. Jurkiewicz and Sanguinetti, *Circ. Res.* 72: 75–83 (1993). Thus, a specific inhibitor of the minK channel would be an effective antifibrillatory or anti-arrhythmic agent. Activators of the minK channel, on the other hand, may be anti-ischemic agents. A need exists, therefore, for methods of screening for inhibitors and/or activators of the minK channel.

BRIEF DESCRIPTION OF THE INVENTION

The present invention concerns a modified *Saccharomyces cerevisiae* cell, wherein the cell expresses a nucleic acid sequence for a minK protein or a functional derivative or mutant thereof but does not express TRK1 and TRK2.

The present invention further concerns a process for detecting modulators of the minK channel, which comprises:

(a) treating modified *Saccharomyces cerevisiae* cells with a test substance, wherein the modified *Saccharomyces cerevisiae* cells express a nucleic acid sequence for a minK protein or a functional derivative or mutant thereof, but do not express TRK1 and TRK2;

(b) detecting any change in growth of the cells after treatment with the test substance.

This process is useful for detecting modulators of the minK channel.

BRIEF DESCRIPTION OF THE FIGURES

FIG. 2 shows the nucleotide (SEQ. ID. NO. 1) and deduced amino acid (SEQ. ID. NO. 2) sequences for TRK1. (Sequence reprinted from Murai et al., *Bioch. Biophys. Res. Comm.* 161: 176–181 (1989), which is incorporated herein by reference). Residues 41 to 72, which define the pore of the protein, are underlined.

FIG. 3 shows the nucleotide (SEQ. ID. NO. 3) and deduced amino acid sequence (SEQ. ID. NO. 4) sequences for TRK2. (Sequence reprinted from Gaber et al., *Mol. Cell. Biol.* 8: 2848–2859 (1988), which is incorporated herein by reference.) In the preferred embodiment described hereinafter, the portion underlined was deleted and replaced by marker gene HIS3.

FIG. 4 shows the nucleotide (SEQ. ID. NO. 5) and deduced amino acid (SEQ. ID. NO. 6) sequences for human minK. (Sequence reprinted from Ko and Gaber, *Mol. Cell. Biol.* 11: 4266–4273 (1991), which is incorporated herein by reference.) In the preferred embodiment described hereinafter, the portion underlined was deleted and replaced by marker gene TRP1.

FIG. 5 shows that growth of transporter mutant strains is potassium-dependent. Tetratype segregants from a cross between MATα trk1::HIS3×MATa trk2::TRP1 were patched onto rich media supplemented with 100 mM KC1. After overnight incubation at 30° C., the plate was replica-printed containg 100 mM, 10 mM or 0.1 mM KC1. Plates were incubated at 30° C. and scored for 48 hours. WT denotes wildtype, Low Aff.- denotes trk2 mutant, High Aff.- denotes trk1 mutant, High and Low denotes trk1, trk2 double mutant.

DETAILED DESCRIPTION OF THE INVENTION

Figure 1A:
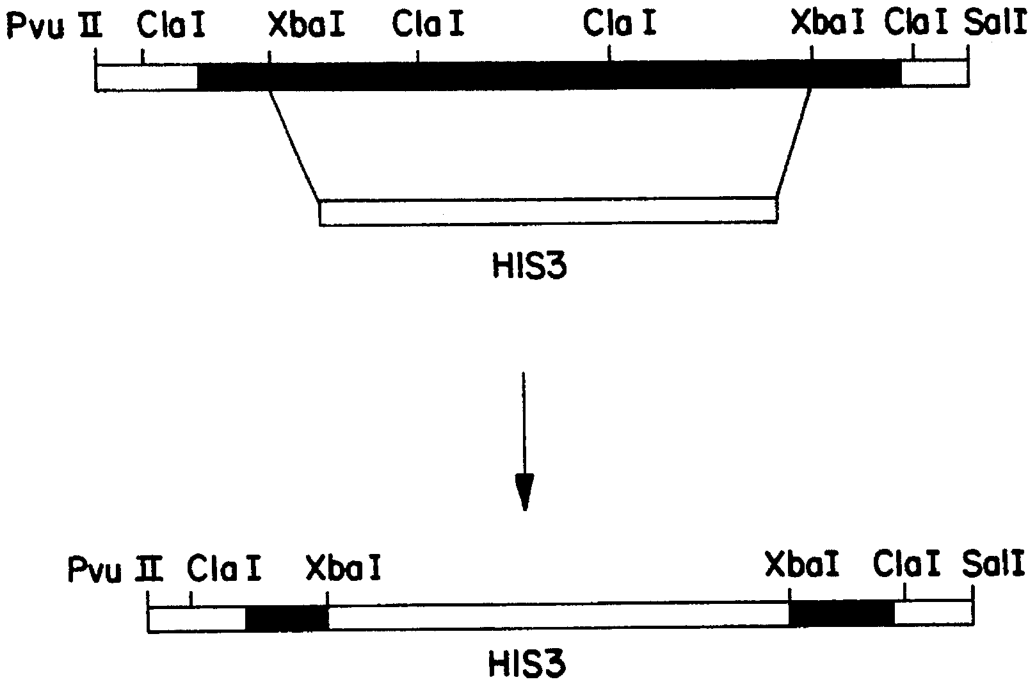
FIG. 1 shows representations of genomic fragments containing the wld type TRK1 and TRK2 loci and the corresponding mutant alleles, trk1::HIS3 and trk2::TRP1. The TRK1 and TRK2 coding regions are indicated by solid lines. The mutant alleles were transformed into a yeast strain to replace the wild type loci.
Figure 1B:
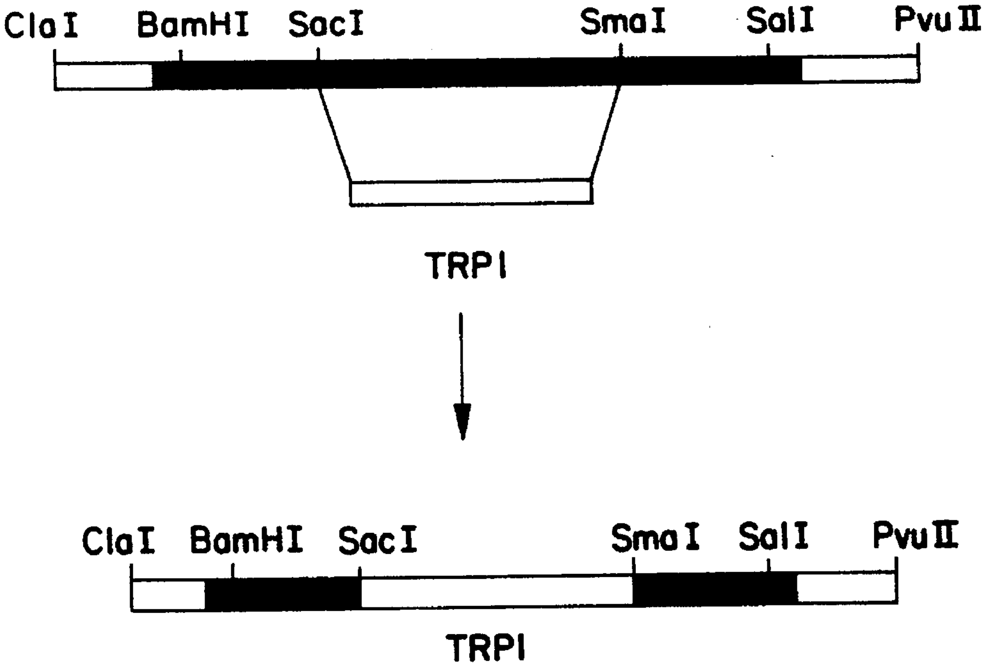

The following definitions apply to the terms as used throughout this specification, unless otherwise limited in specific instances.

The terms "deficient" or "deficiency" as used with respect to a gene refers to an allele altered (e.g., by homologous recombination, resulting in the insertion of foreign sequences) such that either no product or only an inoperative fragment of the wild-type product can be expressed. A "deficient" allele within this definition may also comprise a gene deletion, wherein the gene has been deleted in toto; a gene disruption, wherein the gene is interrupted by another gene or nucleic acid sequence; a partial deletion, wherein one or more bases are deleted; a substitution, wherein one or more bases are replaced by other bases; and other such mutations as will be understood by persons having ordinary skill in the art. Such deletions, disruptions, and substitutions may take place in, for example, the coding region, a promoter, or an enhancer.

The term "modified" as used with respect to a cell refers to a cell in which the wild-type genome has been altered by addition of one or more heterologous genes, a defidency in one or more wild-type genes, or a combination thereof. Such modifications may be carried out by transformation and homologous recombination through techniques well understood by those having ordinary skill in the art.

The term "a minK protein" refers to a protein having at least the smallest portion of the full-length wild-type minK protein that can result in measurable potassium ion transport in *Saccharomyces cerevisiae*. Human minK protein is preferred. Exemplary methods for such measurement of potassium ion transport are described herein. Proteins having residues 41 to 72 of FIG. 2 are preferred for the minK protein.

The term "a functional derivative or mutant thereof" as used with respect to a protein refers to a protein differing from the subject protein by one or more amino acid residues but still having the biochemical function of the protein and greater than about 90% sequence homology. In the case of the minK protein, a "functional derivative or mutant thereof" refers to such proteins that have potassium transport activity but do not have the identical amino acid sequence shown in FIG. 2. Such derivatives and mutants may include proteins that differ from the wild-type protein by amino acid substitutions, deletions, disruptions, and the like. Such differences may be accomplished by genetic means, using such techniques as site-directed mutagenesis or mutagenic PCR prior to translation, or by chemical means, using proteases and/or ligases after translation.

The yeast cell of the present invention begins with a yeast strain having deficient alleles in the TRK1 and TRK2 genes required for potassium uptake. The modified alleles are genetically stable and recessive, so they can be complemented with activities encoded by heterologous genes introduced into the strain.

Biosynthetic marker genes (e.g., HIS3 and TRP1) may be inserted into the loci for the wild-type potassium uptake genes. Such modified alleles may then be transformed into yeast to replace the wild-type loci by homologous recombination. The modified alleles are readily detected by scoring for the presence of the biosynthetic marker. The markers inserted into the transporter loci also provide a simple means of transferring these mutations into other genetic backgrounds.

A strain deficient in one potassium uptake gene (e.g., TRK1) may be crossed with a strain of opposite mating type deficient in another potassium uptake gene (e.g., TRK2). Progeny bearing both genetic deficiencies may be identified by scoring for the presence of both markers.

A variety of potassium ion channels may be introduced into this strain to assess whether these channels can complement the growth defect on potassium-deficient media. Alternatively, the strain may be used to screen gene libraries (e.g., human cDNA libraries) for clones that complement the growth defect. This analysis may reveal potassium ion channels that have been described physiologically but have not yet been cloned. Each application results in a strain expressing a foreign potassium ion channel, useful in a screen for modulators of the channel.

A yeast strain expressing a potassium ion channel can be adapted to natural products screening. A simple screen design involving growth inhibition or potassium ion uptake in agar plates or in liquid culture may detect compounds that modulate channel function. For screening of activators of the potassium ion channel, the screen may include such modifications as metabolic inhibition of calcium, anoxic growth conditions, increased growth rate, or increased potassium ion uptake.

A test substance used in the process of this invention may be, for example, a synthetic compound or a natural product. Such natural products include extracts from plants, animals and microorganisms.

DETAILED DESCRIPTION OF THE PREFERRED EMBODIMENT

Knockout of the high affinity transporter

A mutation in the high affinity potassium transporter, TRK1, began with the isolation of the wild type gene from a yeast genomic library. Large portions of the 5' and 3' ends of the TRK1 coding region (FIG. 3, SEQ. ID. NO. 3) were amplified in polymerase chain reactions, radiolabeled and hybridized to colonies containing the yeast genomic library. Three clones contained the entire TRK1 locus (promoter and coding region) as determined by hybridization to both 5' and 3' fragments. These results were further confirmed by Southern blots and restriction mapping.

The TRK1 gene was subcloned into bacterial vectors, pUC19 and pSL1180. A 2350 bp deletion of the coding region was created by digestion with XbaI. Into this deletion was inserted the yeast biosynthetic gene HIS3. The mutant allele, trk1 ::HIS3, was used to transform yeast strains to histidine prototrophy. Transformants were verified by Southern blots.

Because TRK1 encodes the high affinity potassium ion transporter, the mutant strain should have a growth requirement for potassium. As expected, $His^+$ transformants grew very poorly on media containing 100 μM potassium chloride. The growth defect was remediated by increasing the potassium concentration to 100 mM.

Knockout of the low affinity transporter

Oligonucleotides were used to produce portions of the TRK2 coding region (FIG. 4, SEQ. ID. NO. 5) corresponding to the 5' (600 bp) and 3' (800 bp) ends of the coding region by polymerase chain reaction (PCR) amplification of yeast genomic DNA. The fragments were assembled in pSL1180. The construct was linearized at the junction of the 5' and 3' coding fragments and religated with a fragment containing the yeast TRP1 gene to create trk2::TRP1. This construct lacks 1170 basepairs of the TRK2 coding region and was used to transform a yeast strain to tryptophan prototrophy. Transformants were verified by Southern blots.

Since the TRK2 locus encodes a low affinity potassium ion transporter, the mutant strain does not have a growth phenotype on potassium ion-deficient media.

Formation of the double mutant strain

The high and low affinity transporter mutations were constructed in yeast strains of opposite mating types to facilitate genetic analysis of the mutants and to obtain the double mutant (trk1-, trk2-) strain. Such a cross was carried out between the two strains (MATa, trk1 ::HIS3×MATa, trk2::TRP1).

The diploid strain grew vigorously on all media regardless of potassium concentration, indicating that the mutations are recessive. Recessive mutations are required for complementation with heterologous genes introduced into this strain.

In haploid, the modified alleles marked by the HIS3 and TRP1 biosynthetic marker genes were readily scored and segregated as expected for two unlinked genes. Both markers segregated 2+:2−, and their segregation was independent relative to each other. This result was anticipated, given that TRK1 maps to chromosome 10 and TRK2 maps to chromosome 11. The trkpheno-types (inviable on media with low concentrations of potassium) co-segregated with the appropriate biosynthetic markers, indicating that the introduced mutations mimic the phenotypes described in Rodriguez-Navarro, A. and Ramos, J., *J. Bacteriol.* 159:940–945 (1984); Ramos, J. et al., *Arch. Microbiol.* 143:88–93 (1985); Gaber, R., Styles, C. and Fink, G., *Mol. Cell Biol.* 8:2848–2859 (1988); and Ko, C. and Gaber, R., *Genetics* 125: 305–312 (1990).

Three phenotypes for potassium requirements were expected and observed from segregants of this cross, resulting from the following four genotypes: wild type, low affinity mutant, high affinity mutant, and double mutant (high and low affinity). Physical characterization of the modifications in the four segregants of a tetrad confirmed the segregation results. Southern blots and PCR amplification of the mutant loci with primers that flank the TRK genes produced the expected products.

Rescue of the mutant phenotype

The double mutant strain was transformed with a plasmid (pGAL) containing the wild type TRK1 gene, the heterologous test gene (HminK) or the vector alone. The HminK-transformed strain is a preferred embodiment of this invention and was deposited with the American Type Culture Collection, 12301 Parklawn Drive, Rockville, Md. 20852-1776 or Aug. 27, 1993 and assigned accession number ATCC 74,238. The strain is available upon issuance of a U.S. patent hereon and will be maintained for a period of at least 30 years after the date of deposit, and for a period of at least five years after the most recent request for a sample.

Figure 7A:
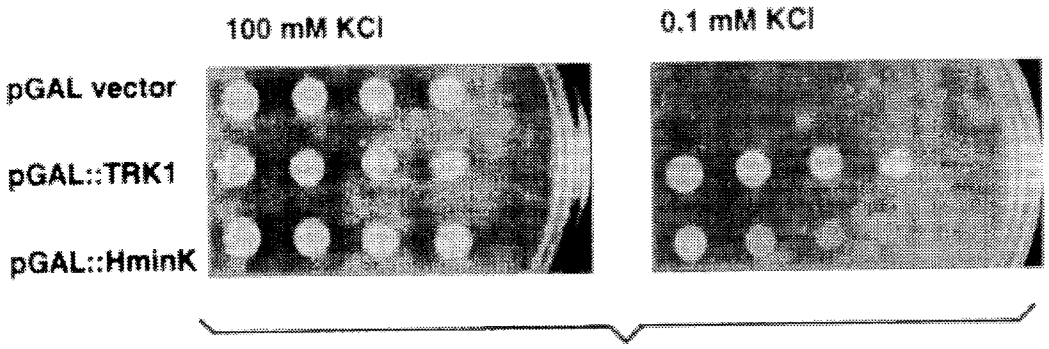
FIG. 7A shows cultures of strains containing the pGAL vector, pGAL::TRK1 or the pGAL::HminK plasmid grown in inducing media (2% galactose) at 30° C. with vigorous aeration and spotted on agar plates containing 100 mM or 0.1 mM KC1. In part B, aliquots of cultures were spotted on agar plates containing clofilium (100 μM) or dofetilide (1 μM). Plates were scored after a 48-hour incubation at 30° C.
Figure 7B:
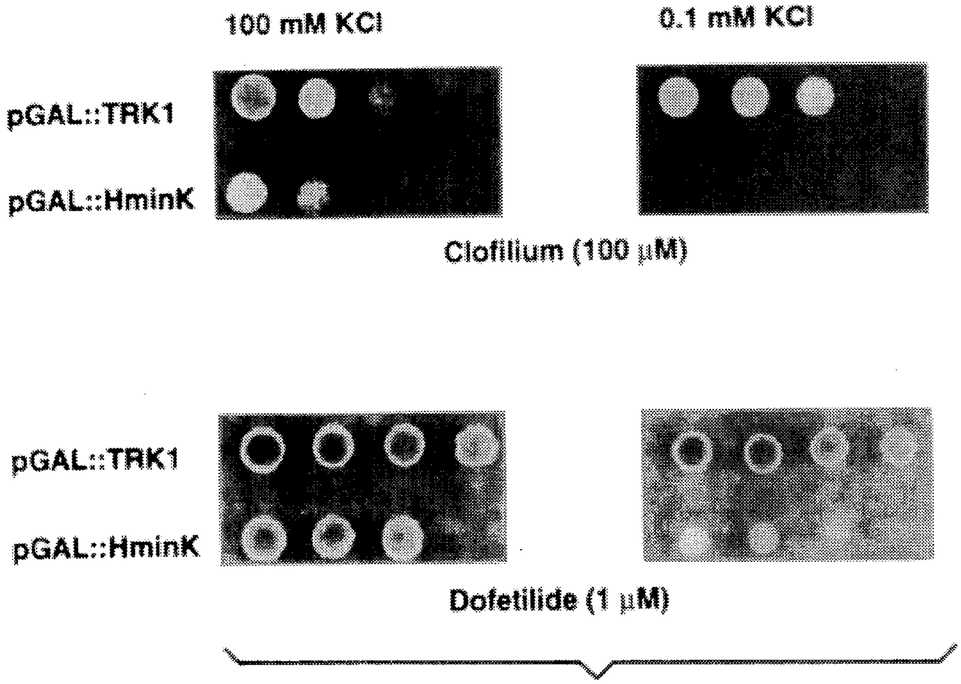

Transformants were diluted serially and spotted onto plates with either high (100 mM) or low (0.1 mM) concentrations of potassium chloride. Plates were incubated at 30° C. for 2 days. As shown in FIG. 7, strains containing either vector, TRK1, or HminK are able to grow at 100 mM potassium chloride, but only the TRK1 or HminK transformed strains grown at 0.1 mM potassium chloride.

Genetic and biochemical verification

Growth measurements of the trk mutants in either potassium-deficient or low pH media are consistent with the phenotypes reported in Gaber, R., Styles, C. and Fink, G., *Mol. Cell Biol.* 8:2848–2859 (1988) and Ko, C. and Gaber, R, *Genetics* 125:305–312 (1990). In media supplemented with potassium chloride, the mutant strains grew in a potassium-dependent manner (FIG. 5).

In another experiment, the double mutant was transformed with pGAL vector including either TRK1 or HminK as described above. The transformed strains were then separately challenged with clofilium (100 μM) and dofetilide (0.1 μM) at 100 mM and 0.1 mM of potassium chloride. As expected, clofilium blocked potassium uptake in the HminK strain but not in the TRK1 strain.

In addition, the HminK gene used in the transformation was sequenced. This analysis, which included sequencing of both strands, revealed a single nucleotide change resulting in the conversion of amino acid 38 from serine to glycine. This mutation is located in the N-terminus and does not appear to affect HminK function.

For further verification, mRNA transcripts were expressed in Xenopus oocytes. The expression products caused potassium ion currents that are blocked by clofilium (50 μM) and kinetically indistinguishable from HminK currents reported in the literature. This result is consistent with the recent report indicating that residues 41 to 72 define the pore of the protein and are sufficient to form channels in lipid bilayers. Ben Efraim et al., *Biochemistry* 32: 2371–2377 (1993). That report further indicates that the region encompassing residue 38 may not be functionally important.

Materials and Methods

Construction of the transporter mutant strain

A. trk1 deletion. TRK1 DNA sequences spanning nucleotides 181 to 4108 were synthesized by PCR amplification using the following oligonucleotides:

5' CCGGATCCATGCATTTTAGAAGAACGATG 3' (SEQ. ID. NO. 7) and

5' ATCGGCATGCGTTGACGATGACGAAAGCAC 3' (SEQ. ID. NO. 8). The product was digested with BamHI and SphI and cloned into pUC19. The plasmid was digested with XbaI to remove nucleotides 610 to 2964 from the coding region. The remaining vector and flanking regions of TRK1 was gel purified and ligated with a fragment containing the HIS3 gene, containing XbaI cohesive ends, to create a deletion/insertion mutation. This plasmid was digested with EcoRI and SphI and then used to transform a haploid yeast strain (MATa ade2-1, can1-100, his3-11,15, leu2-3,112trp1-1,ura3-1) to hisitidine prototrophy using the LiOAC procedure. To confirm the disruption of the TRK1 locus, His+ transformants were assessed by Southern blotting and growth on media lacking potassium.

B. trk2 deletion. Sequences corresponding to the 5' and 3' ends of the TRK2 coding region were obtained by PCR amplification of yeast genomic DNA. The following oligonucleotides were used to produce a portion of the 5' end spanning nucleotides 1016 to 1639:

5' GCGGATCCGTCGACTTCATTTCCGGGTTCT 3' (SEQ. ID. NO. 9) and

5' GCTAGGAGCTCCCGGGTTGGCGCTTACTTGAGAA 3' (SEQ. ID. NO. 10).

The following oligonucleotides were used to produce a portion of the 3' end spanning nucleotides 2729 to 3584:

5' GTCTTAAACGCTACGGATTGGATTC 3' (SEQ. ID. NO. 11) and

5' GCTTCCCCCAAAACTTTGTTGC 3' (SEQ. ID. NO. 12).

The 5' and 3' PCR-amplified products were digested with combinations of SalI and SacI, and SacI and BamHI: respectively. Fragments were gel purified and then ligated in a three-way ligation with vector pSL1180 (Pharmacia; Note that this vector was initially digested with HindIII and EcoRV, endfilled and religated to remove a portion of the polylinker. This modified vector was then digested with SalI and BamHI and gel-purified for the three-way ligation.) The three-way ligation product was digested with SacI and XmaI and ligated with the TRP1 gene, containing SacI and XmaI ends, to create an insertion/deletion mutation. This plasmid was digested with SalI and BamHI and then used to transform a hapioid yeast strain (MATa ade2-1, can1-100,. his3-11.15, leu2–3.112, trp1-1-1, ura3-1) to tryptophan prototrophy. $Trp^+$ transformants were assessed by Southern blotting to confirm the disruption of the TRK2 locus.

C. To create the double mutant trk1D trk2D, a standard cross between transformants containing the trk1::HIS3 mutation and the trk2::TRP1 mutation was performed. The resulting diploid was induced to undergo meiosis and tetrads were dissected onto YPD media supplemented with 100 mM KCl. Complete tetrads were then assessed for segregation of the markers (His and Trp) and for growth on media containing either 100 mM, 10 mM, or 0.1 mM KCl. In tetratype tetrads, the four genotypes produced three phenotypes with respect to growth on potassium-deficient media. This is the expected result for the segregation of the trk1 and trk2 mutations which are unlinked genes. All colonies arising from spores that received both the His and Trp markers grow only on media containing 100 mM KCl, indicating that these colonies were defective in both $K^+$ transporters.

Construction of Expression Plasmids pGAL::HminK. The following oligonucleotides were used to amplify sequences encoding the Human HminK protein from HeLa cell genomic DNA:

5' GCGAATTCAAAAAAAATGATCCT-GTCTAACACCAC 3' (SEQ. ID. NO. 13) and

5' GCTCTAGATCATGGGGAAGGCTTCGTCTC 3' (SEQ. ID. NO. 14). The PCR-amplified product was digested with EcoRI and XbaI gel pudfied and cloned into an identically digested pYES2 vector (Invitrogen). The plasmid was verified by standard restriction digests and the insert was analyzed by DNA sequencing.

pGAL::TRK1. The following oligonucleotides were used to amplify sequences encoding the yeast Trk1 protein from a plasmid containing the TRK1 gene (this plasmid was isolated from a yeast genomic library by hybridization with 5' and 3' DNA fragments unique to the TRK1 gene):

5' CGGGATCCAAAAAATGCATTTTAGAA-GAACGATGAG 3' (SEQ. ID. NO. 15) and

5' CCCGCTCGAGCGATGAGTGGGGATTTTGTC 3' (SEQ. ID. NO. 16). The PCR-amplified product was digested with BamHI: and XhoI, gel purified and cloned into identically digested pYEUra3 vector (Clontech). The plasmid was verified by restriction digests and complements a trk1 deletion mutation when expressed in vivo.

Assay for growth on $K^+$ deficient agar media

Cultures of $K^+$ transporter mutant strains containing either pYES2 vector, pGAL::TRK1 or pGAL::HminK plasmids were grown in inducing media (2% galactose) at 30° C. with vigorous aeration. A. Serial dilutions of each culture were spotted onto agar plates containing either 100 mM or 0.1 mM. KCl. B. Serial dilutions of strains containing pGAL-::TRK1 or pGAL::HminK plasmids were spotted onto agar plates containing 100 μM clofilium or 1 μM dofetilide at both KCl concentrations. All plates were incubated at 30° C. and scored after 2 days.

Assay for growth in the presence of inhibitors

Figure 6:
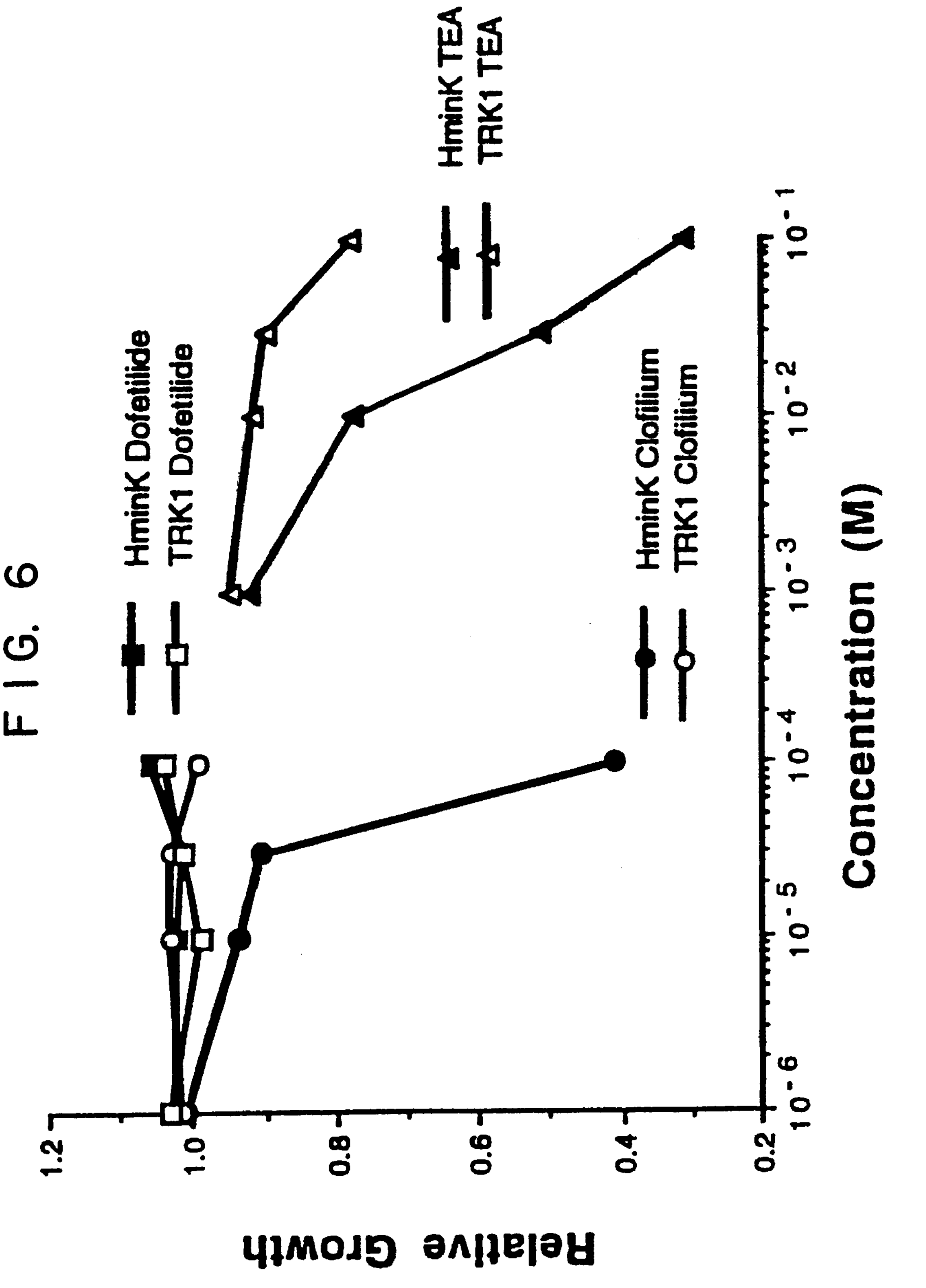
FIG. 6 shows cultures of strains containing the pGAL-::HminK plasmid or the pGAL::TRK1 plasmid grown in inducing media (2% galactose) at 30° C. with vigorous aeration. Inhibitors were added to cultures over a range of concentrations. Samples were removed at various intervals and the optical density at 600 nm was determined. Growth measurements were normalized to values obtained for growth in the absence of drug and are plotted as relative growth versus concentration of drug.

Cultures of strains containing the pGAL::HminK plasmid or the pGAL::TRK1 plasmid were grown in inducing media (2% galactose) at 30° C. with vigorous aeration. Inhibitors were added to cultures over a range of concentrations. Samples were removed at various intervals and the optical density at 600 nm was determined. Growth measurements were normalized to values obtained for growth in the absence of drug and are plotted as Relative Growth versus concentration (FIG. 6). Similar cultures grown in inducing medium were embedded in agar and assessed for growth in presence of the compounds listed in Table 1. Plates were scored after a 48-hour incubation at 30° C.; "+" denotes growth inhibition.

TABLE 1

| Compound | Activity | Inhibition in agar HminK strain | TRK1 strain |
|---|---|---|---|
| clofilium | Class III AA ($I_{KS}$ and $I_{KR}$) | + | − |
| dofetilide | Class III AA ($I_{KR}$) | − | − |
| E-4031 | Class III AA ($I_{KR}$) | − | − |
| quinidine | Class I AA ($Na^+$ and $K^+$) | + | + |
| tetrodotoxin | $Na^+$ channel blocker | − | − |
| TEA Cl | nonselective $K^+$ inhibitor | + | − |
| diltiazem | Calcium entry blocker | − | − |

(AA denotes antiarrhythmic;
+ indicates compound produced a zone on inhibition)

What is claimed is:

1. A modified *Saccharomyces cerevisiae* cell, wherein the cell expresses a nucleic acid sequence for a minK protein but does not express TRK1 and TRK2 wherein the minK protein is capable of conducting an inward potassium ion current.

2. The modified cell of claim 1, wherein the minK protein consists of residues 41 to 72 of SEQ. ID. NO. 6.

3. The modified cell of claim 1, wherein the minK protein has the amino acid sequence of SEQ. ID. NO. 6.

4. The modified cell of claim 1, wherein the minK protein has the amino acid sequence encoded by a nucleic acid having the nucleotide sequence of SEQ. ID. NO. 5.

5. The modified cell of claim 1, ATCC 74,238.

6. The modified cell of claim 1, comprising an expression vector for the minK protein.

7. The modified cell of claim 1, comprising an expression vector for residues 41 to 72 of SEQ. ID. NO. 6.

8. The modified cell of claim 1, comprising an expression vector for a polypeptide having the amino acid sequence of SEQ. ID. NO. 6.

9. The modified cell of claim 1, comprising an expression vector having the nucleotide sequence of SEQ. ID. NO. 5.

10. The modified cell of claim 6, wherein the expression vector is pGAL.

* * * * *